US006856839B2

(12) United States Patent
Litovitz

(10) Patent No.: US 6,856,839 B2
(45) Date of Patent: Feb. 15, 2005

(54) USE OF ELECTROMAGNETIC FIELDS IN CANCER AND OTHER THERAPIES

(75) Inventor: Theodore A. Litovitz, Annapolis, MD (US)

(73) Assignee: Catholic University of America, Washington, DC (US)

( * ) Notice: Subject to any disclaimer, the term of this patent is extended or adjusted under 35 U.S.C. 154(b) by 0 days.

(21) Appl. No.: 10/426,720

(22) Filed: May 1, 2003

(65) Prior Publication Data

US 2003/0195594 A1 Oct. 16, 2003

Related U.S. Application Data

(62) Division of application No. 09/737,546, filed on Dec. 18, 2000.
(60) Provisional application No. 60/179,738, filed on Feb. 2, 2000.

(51) Int. Cl.[7] ................................................. A61F 2/00
(52) U.S. Cl. ...................................... 607/100; 607/102
(58) Field of Search ................................. 607/100, 115, 607/102, 96, 101, 88; 606/13, 32, 33, 34; 661/35; 604/291

(56) References Cited

U.S. PATENT DOCUMENTS

| | | | | | |
|---|---|---|---|---|---|
| 4,800,899 | A | * | 1/1989 | Elliott | 607/156 |
| 4,815,446 | A | * | 3/1989 | McIntosh | 600/3 |
| 5,450,859 | A | | 9/1995 | Litovitz | |
| 5,544,665 | A | | 8/1996 | Litovitz | |
| 5,566,685 | A | | 10/1996 | Litovitz | |
| 5,780,971 | A | * | 7/1998 | Dawson et al. | 315/39 |
| 5,968,527 | A | | 10/1999 | Litovitz | |
| 6,142,939 | A | * | 11/2000 | Eppstein et al. | 600/309 |
| 6,238,872 | B1 | * | 5/2001 | Mosseri | 435/7.1 |
| 6,246,912 | B1 | | 6/2001 | Sluijter et al. | |
| 6,251,128 | B1 | | 6/2001 | Knopp et al. | |
| 6,259,952 | B1 | | 7/2001 | Sluijter et al. | |
| 6,301,506 | B1 | * | 10/2001 | den Boer et al. | 607/100 |
| 6,331,774 | B1 | * | 12/2001 | Stern | 324/300 |
| 6,451,013 | B1 | * | 9/2002 | Bays et al. | 606/27 |
| 6,561,968 | B1 | * | 5/2003 | Dissing et al. | 600/13 |
| 6,595,934 | B1 | * | 7/2003 | Hissong et al. | 601/3 |

OTHER PUBLICATIONS

Gordon SA, et al., "Induction of heat shock protein 70 protects thymocytes against radiation–induced apoptosis," Arch. Surg. 1997; 132:1277–82.

Ueno S. et al. "Vectorial magmatic stimulation or the human brain." in Electricity and Magnetism in Biology and Medicine, Blank M. Ed. San Francisco Press. Inc. CA. p. 733–4, 1993.

Walker DM, et al., "Heat stress limits infarct size in the isolated perfused rabbit heart," Cardiovose. Res. 1993;27:962–967.

Watters D, "Molecular mechanisms of ionizing radiation–induced apoptosis." Immunol. Cell Biol. 1999;77;263–71.

Aquino DA, et at., "Multiple sclerosis: altered expression of 70–and 27–jDa hear shock proteins in lesions and myelin," J. Neuropathol. Exp. Neurol. 1997;56(6):664–672.

Birnbaum G, et al., "Heat shock or stress proteins and their role as auto–antigens in multiple sclerosis," Ann. NY Acad. Sci. 1997;835:157–167.

Blank M, et at., "Changes in polypeptide distribution stimulated by different levels of electromagnetic and thermal stress," Bioelectrochemistry and Bioenergetics 1994;33:109–114.

(List continued on next page.)

Primary Examiner—Daniel Robinson
(74) Attorney, Agent, or Firm—Jagtiani + Guttag

(57) ABSTRACT

Methods and apparatus are described for the treatment of diseases by exposures to electromagnetic fields. Also, apparatus is described for focusing the biological effectiveness of such fields on specific cells, tissues or organs of a human or animal body.

15 Claims, 12 Drawing Sheets

OTHER PUBLICATIONS

Figure 12:
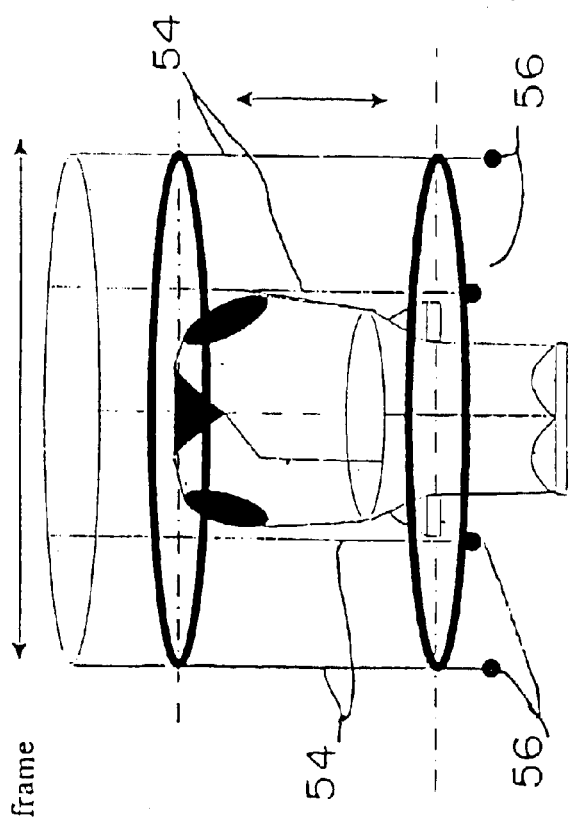

Boehncke WH, et at., "Differential expression heat shock protein 70 (HSP7O) and heat shock cognate proteins 70 (HSC7O) in human epidermis," Arch. Dermatol. Res. 1994; 287(l):68–71.

Borrelli Mi, eta!., "Thermotolerance expression in mitotic CHO cells without increased translation of heat shock proteins," J. Cell Physiol. 1988;169:420–8.

Cadossi R, et a!., "Effect of low frequency low energy pulsing electromagnetic fields on mice injected with cyclophosphamide," Exp. Hematol. 1991;19:196–201.

Chang BK, el a!., "Inhibition of DNA synthesis and enhancement of the uptake and action of methotrexate by low–power–density mucrowave radiation in L1210 leukemic cells," Cancer Res. 1980;40:1002–l005.

Currie RW, et al., "Heat–shock response is associated with enhanced postischemic ventricular recovery" Circ.Res. 1988;63:543–549.

Detlavs I, et al., "Experimental study of the effects of radiofrequency electromagnetic fields on animals with soft tissue wounds," Sci.Total.Environ. 1996;180:35–42.

Di Carlo AL, et al., Myocardial protection conferred by electromagnetic fields,) Circulation 1999;99:813–816.

Di Carlo AL, et al., "Short–Term Magnetic Field Exposures (60 Hz) Induce Protection Against Ultraviolet Radiation Damage," lnt.J.Radiat.Biol. 1998;75: 1541–1550.

Dindar H, et al., "The effect of electromagnetic field stimulation on corticosteroidsinhibited intestinal wound healing," Tokai.J.Exp.Clin.Med. 1993; l8:49–55.

Donnelly TJ, el al., "Heat shock protein induction in rat hearts. A role for improved myocardial salvage after ischemia and reperfusion?," Circulation 1992;85:769–778.

Essele KP, at al., "Coil optimization for neural stimulation with magnetic field," in Electricity and Magnetism in Biology and Medicine, Blank M, Ed. San Francisco Press, Inc. CA. p. 736–7, 1993.

Fitzsimmons RJ, et at., "Embryonic bone matrix formation is increased after exposure to a low–amplitude capacitively coupled electric field, in vitro," Biochim. Biophys. Acta 1986;882:51–56.

Fuks Z, et al., "Basic fibroblast growth factor protects endothelial cells against radiation–induced programmed cell death in vitro and in viva," Cancer Res. 1994;54:2582–90.

Goodman R, et al, "Increased levels of HSP7O transcripts induced when cells are exposed to low frequency electromagnetic fields," Bioelectrochemistry and Bioenergetics I 994;33: 115–120 Gordon, SA, et al., "Induction of heat shock protein 70 protects thymocytes against radiation–induced apoptosis," Arch. Surg. 1997; 132:1277–82.

Han L, et al., "Application of magnetic field–induced heat shock protein 70 for presurgical cytoprotection," J.Cell Biochem. 1998;71 :577–583.

He L et al., "Variation of heat shock protein 70 through the cell cycle in HL–60 cells and its relationship to apoptosis," Exp. Cell Res. 1997;232:64–71.

Hutter MM, at al., "Heat–shock protein induction in rat hearts. A direct correlation between the amount of heat–shock protein induced and the degree of myocardial protection," Circulation 1994;89:355–360.

Iwak K, et al., "Induction of HSP7O in cultured rat neonatal cardiomyocytes by hypoxia and metabolic stress," Circulation 1993;87:2023–2032.

Kang KI, et al., "Luciferase activity and synthesis of Hsp7O and Hsp9O are insensitive to 50Hz electromagnetic fields," Life Sci. 1998;63:489–97.

Korner G, et al., "Effects of ionizing irradiation on endothelial cell transqlutaminase," FEBS Lett. 1993;330:41–5.

Lin H, et al.,"Electromagnetic field exposure induces rapid, transitory heat shock factor activation in human cells" J.Cell Biochem. 1997;66:482–488.

Martin DF, et al., "Radiation sensitivity of cultured rabbit aortic endothelial cells," IJROBP 1984;10:1903–6.

Matsumoto H, et al., "Suppression of heat–induced p53 accumulation and activation by CDDP orx–rays in human glioblastoma cells," Int. J. Oncol. 1998;13(4):741–7.

McCleary VL, et al., "Low magnetic field effects on embryonic bone growth," Biomed.Sci.lnstrum. 1991;27:205–217.

McMillan DR, et al., "Targeted disruption of heat shock transcription factor I abolishes thermotolerance and protection against heat–inducible apoptosis," J. Biol. Chem. 11998;273:7523–8.

Mestril R, el al., "Expression of inducible stress protein 70 in rat heart myogenic cells confers protection against simulated ischemia–induced injury," J.Clin.lnvest. 1994;93:759–767.

Mestril R, et al., "Heat shock proteins and protection against myocardial ischemia," J.Mol.CellCardiol. 1995;27:45–52.

Miyakoshi, J.M., et al., "Long–term Exposure to a Magnetic Field (5 mT at 60Hz) Increases X–ray–induced Mutations," J. Radiat. Res., 1999;40: 13–21.

Morimoto R, et al., "Cell–specific expression of heat shock proteins in chicken reticulocytes and lymphocytes," J.Cell Biol. 1984;99: 1316–1323.

Ormote Y, et al., "Treatment of experimental tumors with a combination of a pulsing magnetic field and an antitumor drug," Jpn. J. Cancer Res. 1990;81:956–961.

O'Rourke JF, et al., "X–irradiation–and carcinogen–induced proteins in cultured CHO cells," Biochem. Soc. Trans. 1992;20(l):745.

Pasquinelli P, et al., "Biological effects of PEMF (pulsing electromagnetic field): An attempt to modify cell resistance to anticancer agents," J. Environ. Pathol. Toxicol. Oncol. 1993;12(4):193–197.

Qi F, et al., "Functional and morphological damage of endothelium in rabbit ear artery following irradiation with cobalt 60," Br. J. Pharmacol. 1998;123:653–60. Ritossa FM,"A new puffing pattern induced by heat shock and DNP in Drosophila," Esperentia 1962;18:571–573.

Ruiter GA, et al., "Alkyl–lysophospholipids activate the SAPKIJNK pathway and enhance radiation–induced aotosis," Cancer Res. 1999;59:2457–63.

Salvatore JR. et al., "Non–ionizing electromagnetic radiation: A study of carcinogenic and cancer treatment potential," Rev. Environ. Health 1994; 10(3–4): 197–207.

Samali A, et al., "Heat shack proteins increase resistance to apoptosis," Exp. Cell Res. 1996;223(l): 163–170.

Schett G, et al., "Enhanced expression of heat shock protein 70 (hsp7o) and heat shock factor 1(HSFl) activation in rheumatoid arthritis synovial tissue," J. Clin. Invest. 1998;102(2):302–311.

Strasser A, et al, "Bcl–2 and thermotolerance cooperate in cell survival," Cell Growth Differ. 1995;6:799–805.

Svedenstal, B.–M.. et al., "Lymphoma development among mice exposed to X–rays and pulsed magnetic fields," Int. J. Radiat. Biol., 1993, vol. 65, No. 1, 119–125.

Szigeti G, et al., "Effects of Bimoclomal, the novel heat shock protein co-induced, in dog ventricular myocardium," Life Sci. 2000;67:73–79.

Tosi P, et al., "Reduction of heat-shock protein-70 after prolonged treatment with retinoids: biological and clinical implications," Am.J. Hematol. 1997;56(3):143–150.

Trautinger F, et al., "Over expression of the small heat shock protein, hsp27, confers resistance to hyperthermia, but not to oxidative stress and UV–induced cell death, in a stably transfected squamous cell carcinoma cell line," J. Photochem. Photobiol. B 1997;39:90–5.

Tyrrell RM, "UV activation of mammalian stress proteins," EXS 1996;77:255–271lJeno 5, et al., "Vectorial magnetic stimulation of the human brain," in Electricity and Magnetism in Biology and Medicine, Blank M, Ed. San Francisco Press, Inc. CA. p. 733–4, 1993.

Walker DM, et al., "Heat stress limits infarct size in the isolated perfused rabbit heart," Cardiovasc.Res. 1993;27:962–967.

Walleczek, J., et al, "Increase in Radiation–Induced HPRT Gene Mutation Frequency after Nonthermal Exposure to Nonionizing 60 Hz Electromagnetic Fields," Radiation Research 151, 489–97 (1999).

Walter RJ, el al., "60–Hz electric fields inhibit protein kinase C activity and multidrug resistance gene (MDRI) up–regulation," Rad. Res. 1997; 147:369–75 Watters D, "Molecular mechanisms of ionizing radiation–induced apoptosis," Immunol. Cell Biol. I 999;77:263–71.

Xu M, et al., "Intracellular distribution of hsp7o during long duration moderate hyperthermia," tnt. J. Hyperthermia 1998;14:211–25.

* cited by examiner

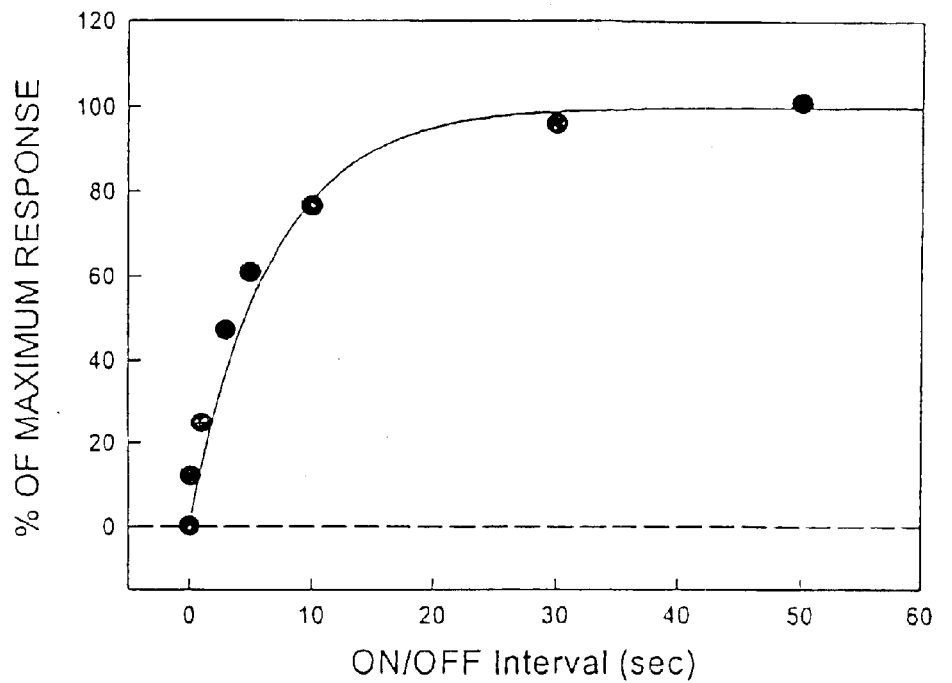
FIG. 1.
Effect of on/off 60 Hz EM fields on hypoxia protection induced in chick embryos
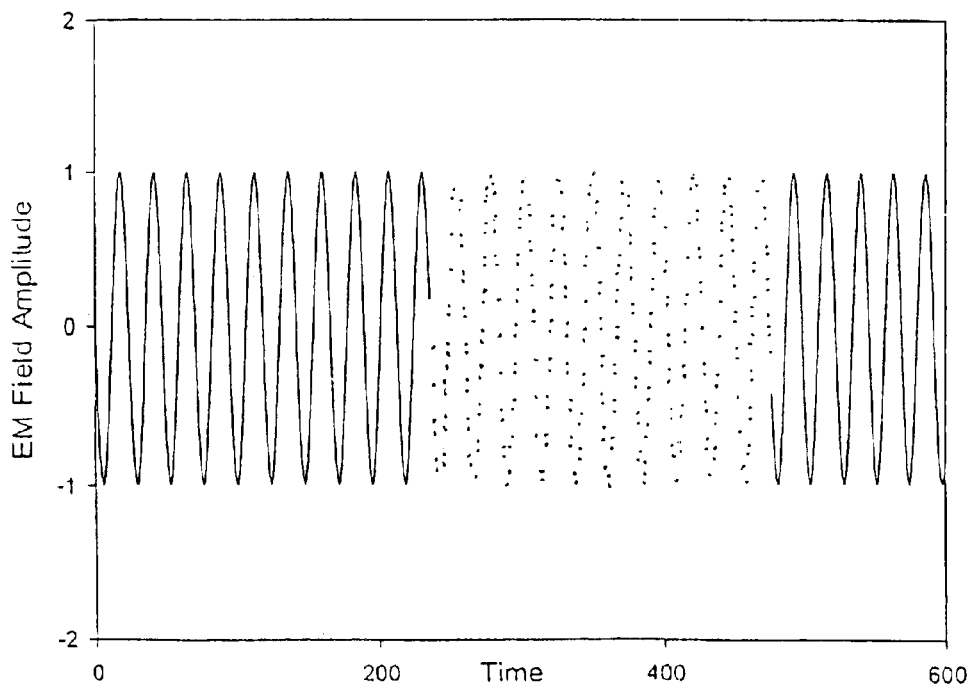
FIG.2. Superposition of EM Fields From 2 Coils
(Equal Field Amplitudes; Alternate on/off Times)
Solid Line = Coil A    Dotted line = Coil B FIG. 3. Superposition of EM Fields From 2 Coils
(Unequal Field Amplitudes; Alternate on/off Times)
Light Solid Line = Coil A    Dark Solid Line = Coil B
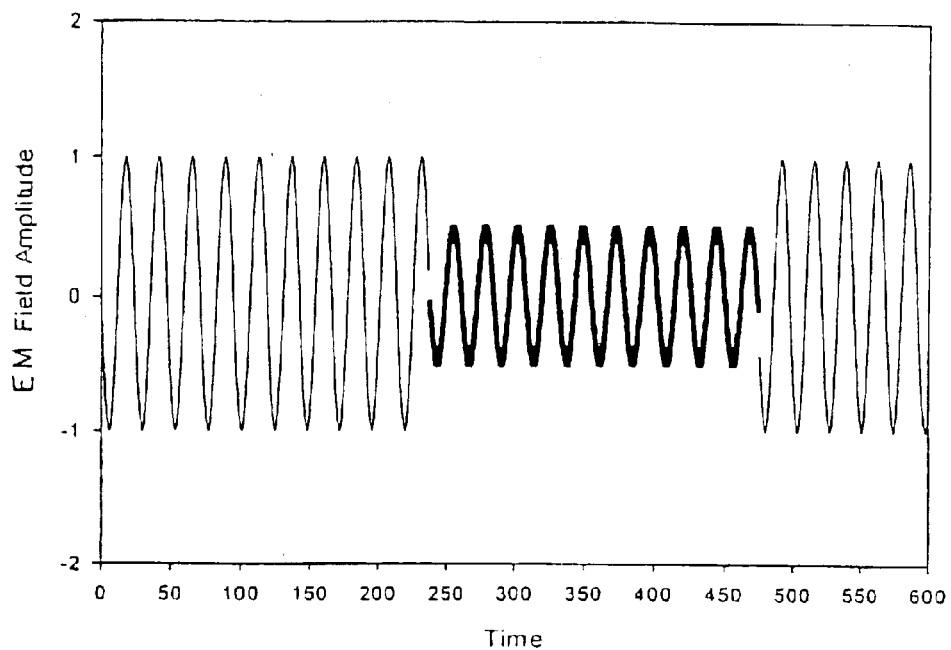
FIG. 4. EM Fields of Helmholtz Coils And A Single Coil Plotted As A Function of Depth Into The Tissue
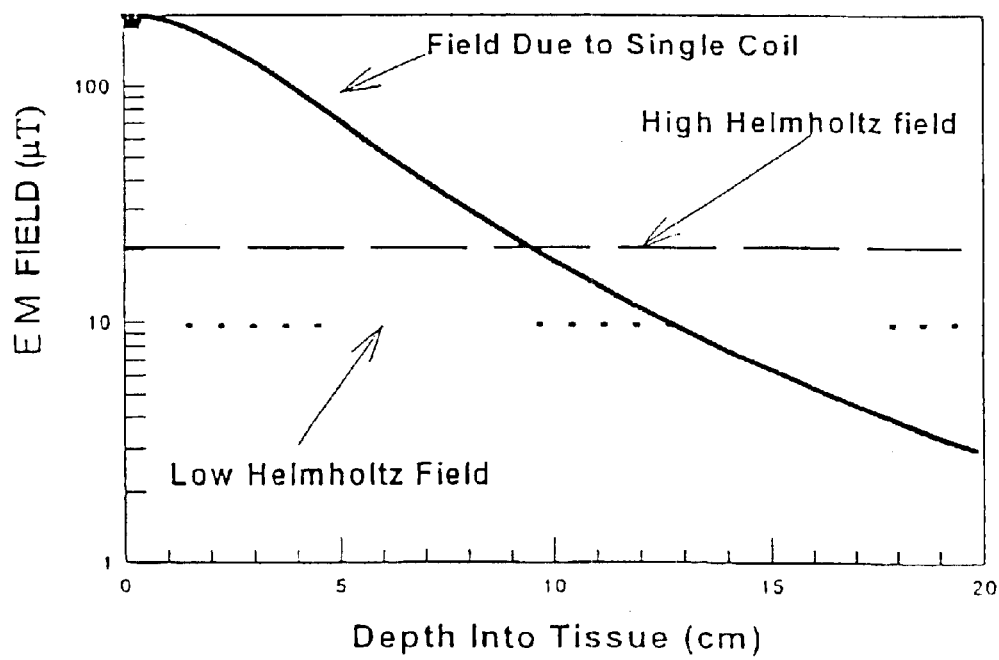

FIG.5. FOCUSING EFFECT OF TWO
ALTERNATELY PULSING EM FIELDS
HIGHER PEAK HELMHOLTZ FIELD
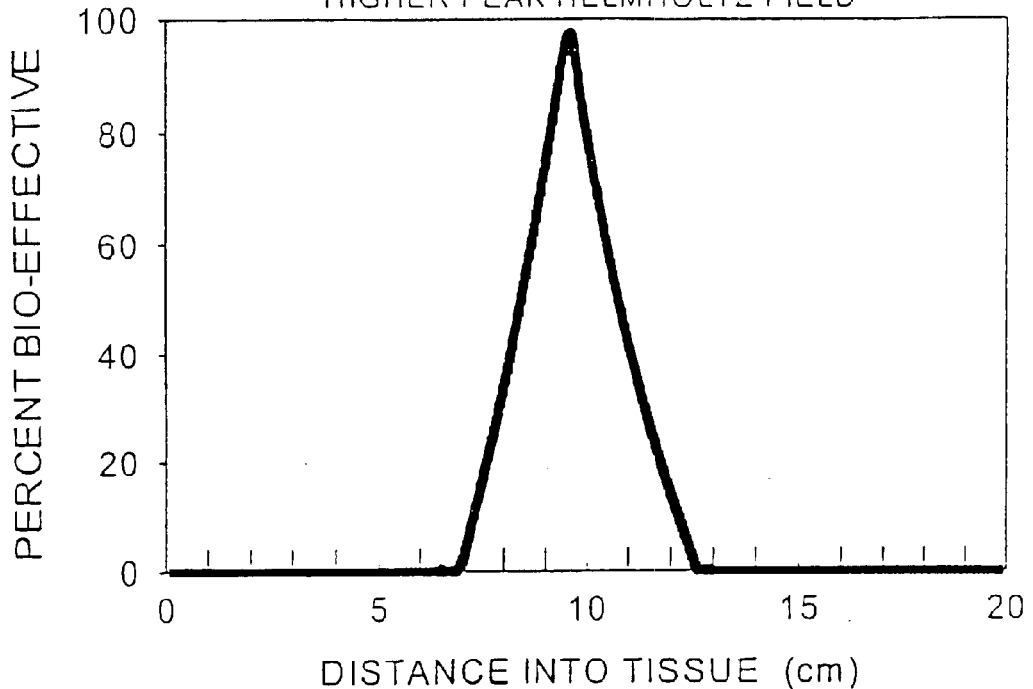
FIG.6.
BROADER FOCUS REGION FROM
Two Alternately Pulsing EM Fields
One Field Source Alternately Increasing and then
Decreasing in Amplitude by a Factor of 2 Every 20 Seconds
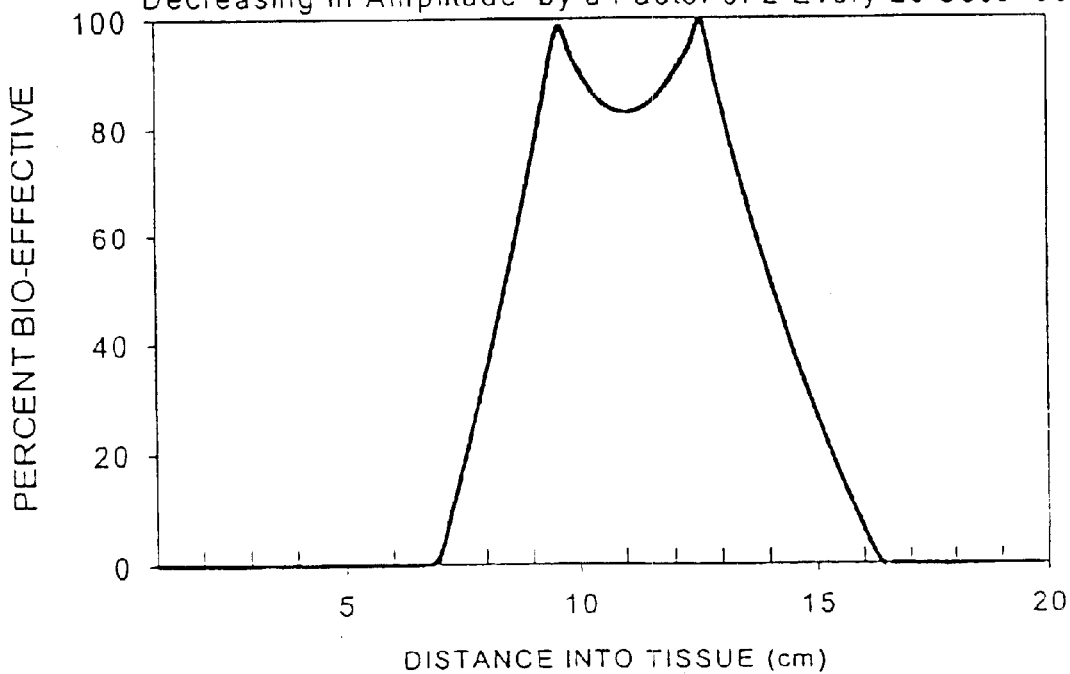

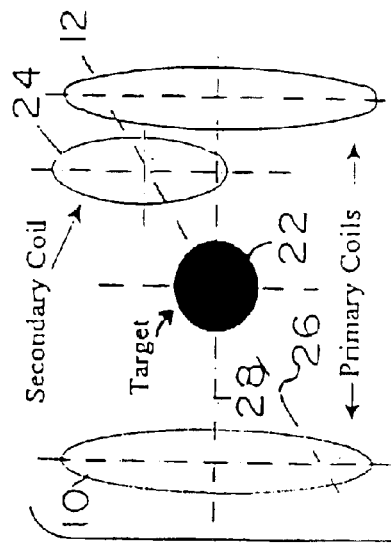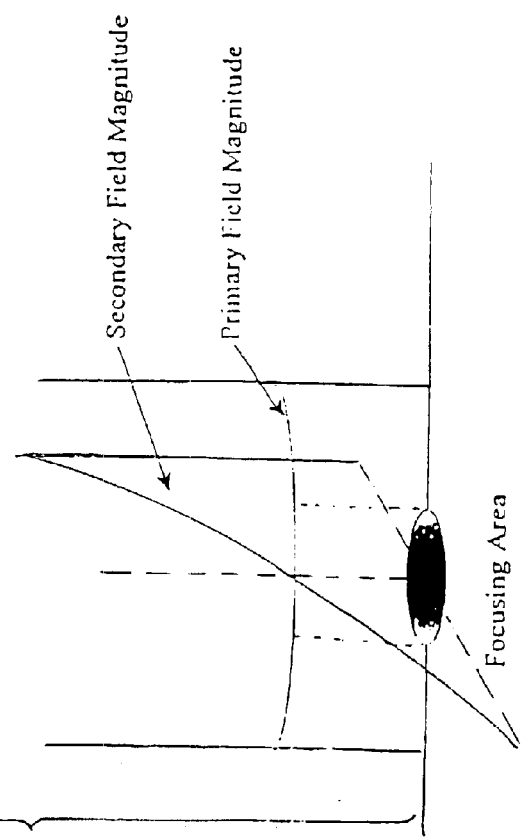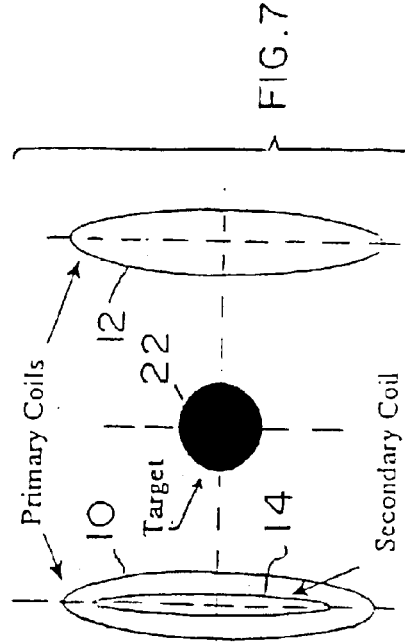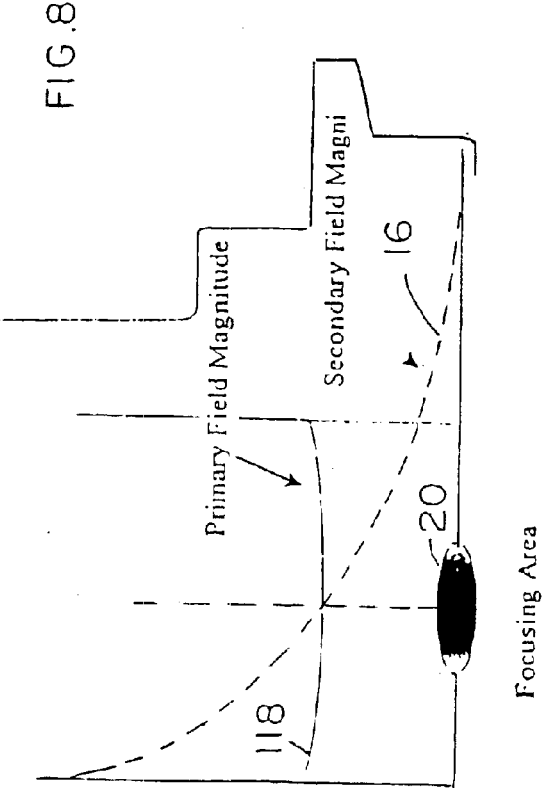
FIG.7
FIG.8

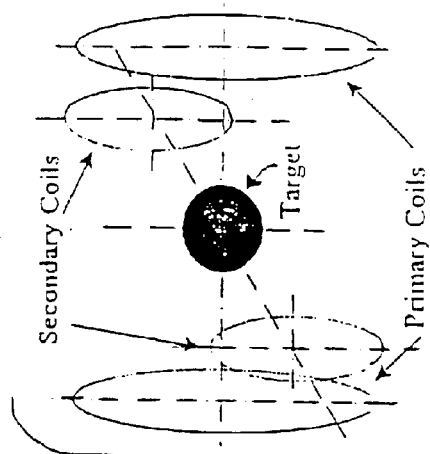
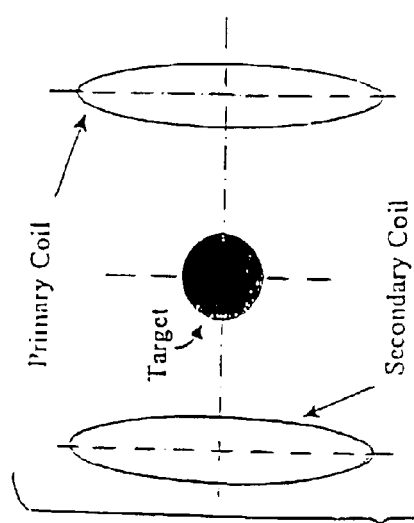
FIG. 9.
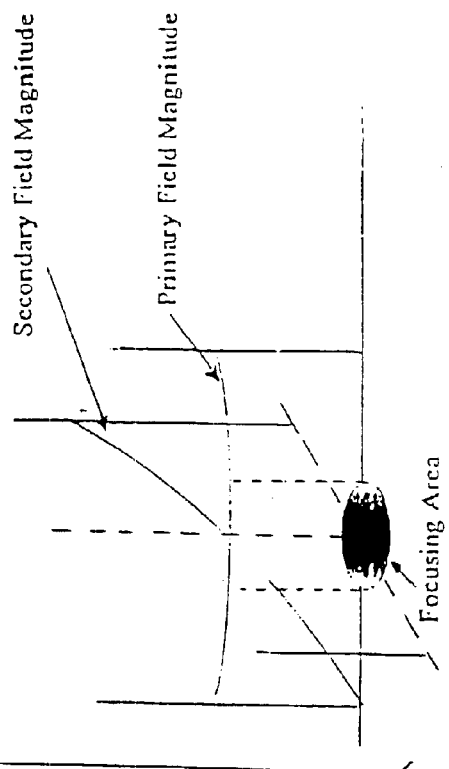
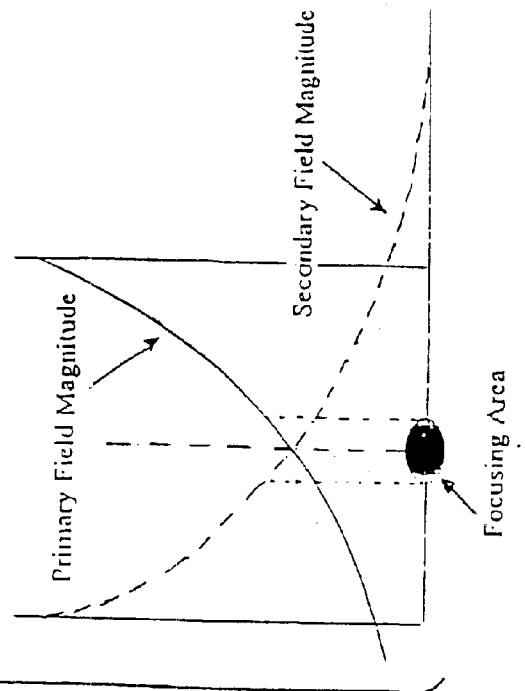
FIG. 10.

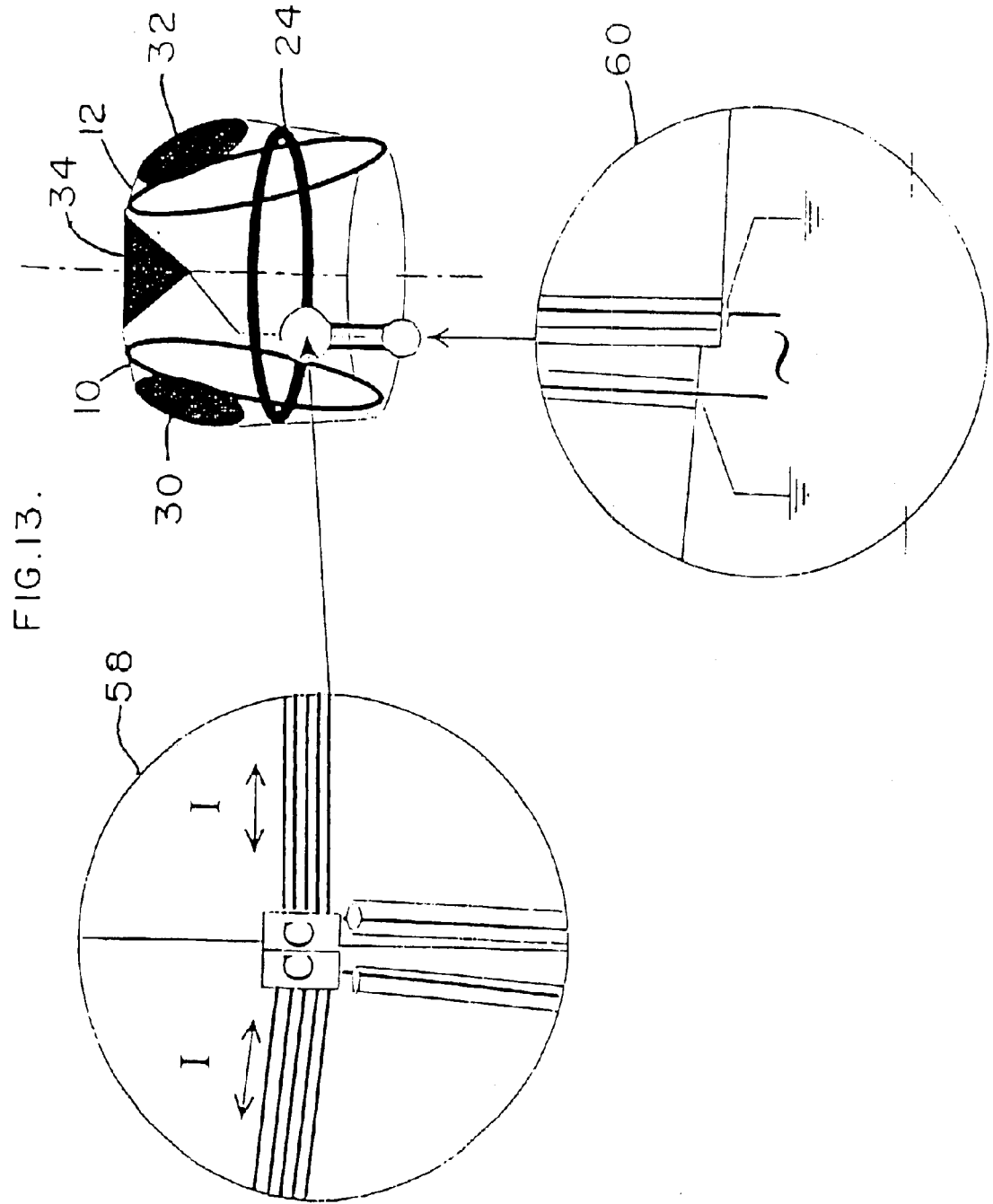

Figure 15:
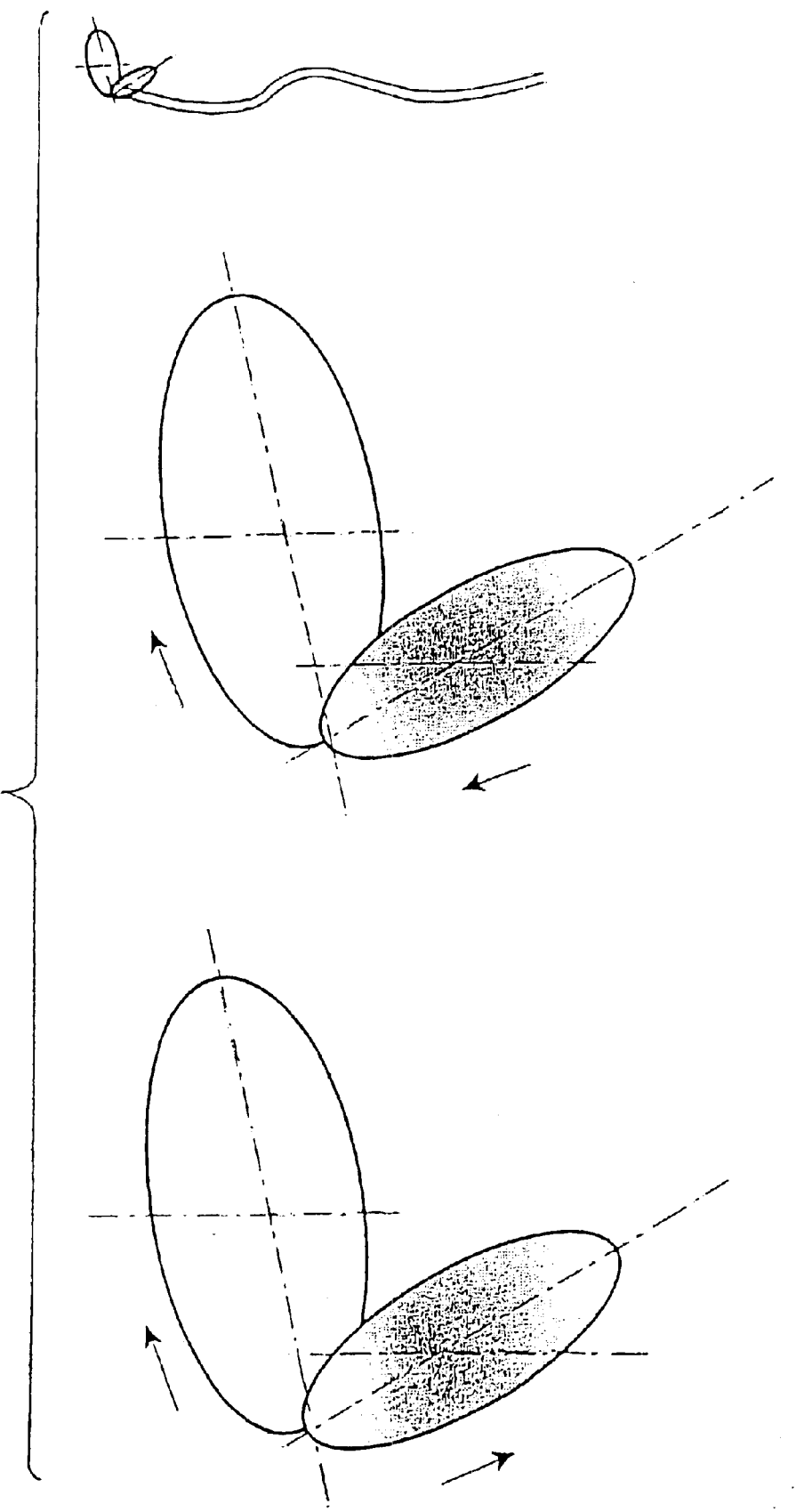

FIG.15. Complex Devices example #5

USE OF ELECTROMAGNETIC FIELDS IN CANCER AND OTHER THERAPIES

BENEFIT OF EARLIER APPLICATION

This application is a divisional application of and claims priority to U.S. patent application Ser. No. 09/737,546, entitled "Use of Electromagnetic Fields in Cancer and Other Therapies" filed Dec. 18, 2000, which claims priority to U.S. Provisional Patent Application No. 60/179,738, filed Feb. 2, 2000. The entire disclosures and contents of the above-identified patent applications are hereby incorporated by reference.

BRIEF DESCRIPTION OF INVENTIONS DESCRIBED AND CLAIMED HEREIN

Methods and apparatus are described and claimed for the treatment and prevention of diseases by exposures to electromagnetic (EM) fields. Also, apparatus is described and claimed for focusing the biological effectiveness of such fields on specific cells, tissues or organs of a human or animal body.

DISCUSSION OF FIELD OF THE INVENTIONS

The inventions described herein relate to the control of heat shock proteins for the treatment of disease. The control is by application of EM fields. The diseases include the treatment of cancer and autoimmune diseases. The inventions are related to the induction by EM fields of the heat shock (stress protein) response, which has been implicated in a number of diseases. I have discovered that although short-term exposures enhance the stress response in cells, long-term exposures have the opposite effect. I also have discovered that long-term EM field exposures can be used to down-regulate the normal stress response and render cells more sensitive to damage from a secondary stress. The ability of EM fields to decrease a body's stress response makes these fields ideal candidates for the treatment of a number of diseases.

The inventions include methods and apparatus that improve the efficacy of any cancer therapy. The inventions involve the application of EM fields, with particular exposure parameters to be described, to selectively increase biological cell sensitivity to any therapeutic agent used to destroy cancer cells (for example, ionizing radiation, chemicals, drugs, etc). These EM fields could be applied to volumes of tissue in which there are biological cells targeted for destruction by a cancer therapeutic agent or agents. For example, the EM fields might be applied to solid tumors, to organs, to regions of the body in which cancerous cells are suspected to exist, or to the body or skin as a whole. These inventions would be used as an adjuvant to cancer therapeutic agents, facilitating or modifying the action of those agents. This would, for example, allow a reduced dose of a therapeutic agent to have the same effect as the usual dose; or for the usual dose to have a more potent effect.

The methods and apparatus described herein can also be used to treat autoimmune diseases, including, but not limited to, multiple sclerosis, arthritis, diabetes, and psoriasis. Autoimmune diseases are among the most insidious and difficult diseases to treat and cure, because they turn the body's immune system against its own tissues. Expression of stress proteins on the surface of cells (these are normally found only in the interior of the cell) can trigger an attack on a cell by the primary defenders in the immune response. In normal cells the stress proteins do not appear on the surface of the cell. In diseased cells they can appear. In autoimmune disease such as multiple sclerosis, in abnormal or diseased cells (e.g. the cells that provide the myelin sheath around nerves), stress proteins are incorrectly processed and thus appear on the cell membrane or cell surface. This triggers the destruction of these otherwise-normal cells by cells of the immune response system. My discovery in this connection is that, under certain conditions, EM fields can down-regulate (i.e. reduce the production of stress proteins). This translates into fewer stress proteins on the cell surface and less destruction. Thus, appropriate EM field exposure can be used to slow the progress of autoimmune disease and, in some cases, allow for the repair of the damage caused by the disease.

The herein inventions would have a significant impact. For 1999, the estimated new invasive cancer cases in the US number 1.2 million, resulting in 563,000 deaths. In addition, new basal and squamous cell skin cancers are estimated to be another 1 million. In 1990, 8.1 million new cancers were estimated throughout the world, with 5.6 million related deaths. In addition, autoimmune diseases afflict huge numbers of people in the U.S. alone (e.g. multiple sclerosis—1,400,000; psoriasis—3,000,000; diabetes—21,000,000; arthritis—81,000,000).

Current cancer therapy is predominantly accomplished by surgery, radiation therapy and chemotherapy. Radiation therapy relies on the deposition of ionizing radiation in the cells and the resulting cytotoxic effects. Chemotherapeutic agents include alkylating agents, anti-metabolites, anti-tumor antibiotics, plant alkaloids, hormones and hormone antagonists, and other miscellaneous agents.

There are many variables affecting any form of cancer therapy that must be taken into account in the art. However, a universal principle is that the more dose of any agent that can be delivered to a target volume, or the more effective that dose can be made to be, the more likely a cancer will be cured, locally controlled or delayed in its progress. The predominant limiting factor is the tolerance of the non-targeted or normal tissues in the vicinity of the target region, in intervening regions, or in the body as a whole.

Methods allowing for delivery of more dose to a target volume, or for improving its effect therein; or methods selectively sparing non-cancerous or normal tissues, or for decreasing the effect there are said to improve the "therapeutic advantage" of a therapeutic agent. Using radiation therapy as an example, a typical way to express this concept, found in any complete text on the art, is a graph of tumor-control-probability and normal-tissue-complication-probability versus dose. Therapeutic advantage is related to the separation of these curves. Factors that increase the separation improve the therapeutic advantage.

I have discovered that, under certain conditions, EM fields can make biological cells and tissues more susceptible to many forms of deleterious stimuli. These include, but are not limited to, a number of deleterious stimuli deliberately applied as therapeutic agents. Thus, I have discovered devices and methods to apply EM fields to selected tissue volumes in humans and animals that will improve the therapeutic advantage of agents used in cancer and other therapies.

Throughout this application the term electromagnetic or EM field is meant to include such fields ranging in frequency from approximately 10 Hz to 5 GHz. The effects described in this application can be obtained using EM fields throughout this frequency region. The choice of the type of source of EM field to be used will be determined by the simplicity and cost of application for a particular therapy.

The herein inventions would be beneficial alone or in combination with other art that uses EM fields to reduce biological cell susceptibility to deleterious stimuli such as the cancer therapies or their side effects (U.S. Pat. No. 5,968,527) ('527). These methods to reduce sensitivity, that is, protect cells, would be targeted to volumes of normal or non-cancerous tissue in which the damage caused by the treatment is to be minimized. Thus, for example, it is expected that exposure of the tissue volumes to the proper sequence of EM fields will allow for both the shift of the tumor-control-probability to lower doses (this application) and the shift of the normal-tissue-complication probability curve to higher doses ('527). That is to say, it would make the cancerous tissue more sensitive to the toxic stimulus and make the normal tissue less sensitive to the toxic stimulus used in the therapy.

It will be obvious to a person skilled in the art upon reading the herein description that these techniques could be applied to other medical procedures using deleterious stimuli which are intended to destroy or modify the biological cells in a chosen volume of tissue for a reason other than cancer therapy. For example, benign growths, keloids, arterio-venous malformations, benign prostatic hyperplasia, splenomegaly, etc.

DESCRIPTION OF RELATED ART

I have earlier received U.S. Pat. Nos. 5,450,859 ('859), 5,544,665 ('665), 5,566,685 ('685) and the aforesaid U.S. Pat. No. 5,968,527 ('527). Of these, '859, '665 and '685 relate to my discovery that harmful effects of a low frequency field (e.g., an EM field) on cells may be avoided by changing one or more characteristic parameters of the field within time intervals of ten seconds or less. No. '527 relates to my discovery that irreversible injury or mortality in a cell caused by an adverse condition may be combated by exposure to an EM field for limited time periods. The relevance of these patents will be further discussed below.

Stress Proteins

Organisms protect themselves against harmful stimuli by activation of a number of different cellular protection pathways. Among these is the classical heat shock response, in which heat shock proteins (hsps) are synthesized (Morimoto and Fodor, 1984). In 1962, Ritossa noted that following application of heat stress there was puffing activity at certain gene loci on *Drosophila* polytene chromosomes, and that this activity was accompanied by enhanced synthesis of a specific family of proteins (Ritossa, 1962). Subsequently, such heat shock response has been shown to occur in all organisms examined. The hsps, which are a class of stress proteins, are a family of molecular chaperones which are induced by a variety of environmental stresses such as heat, chemicals, hypoxia (low oxygen), incorrect glucose levels, heavy metals and amino acid analogs. Throughout this application the terms heat shock proteins (or hsp) and stress proteins shall be used interchangeably. I have found that EM fields ranging from as low as 20 to 30 Hz to as high as 1 GHz can induce this cellular mechanism for protection. The stress proteins so induced are not related to any rise in temperature caused by the EM fields. These stress proteins contribute to protection from and adaptation to cellular stress and are responsible for the repair of damaged proteins.

Pre-Conditioning

Activation of the heat shock stress response pathway can yield beneficial effects from the production of stress proteins, which are long-lasting (effective for up to 24 hours following induction). This finding has led many researchers to search for ways to harness these beneficial effects as a means to protect cells and tissues against the effects of a damaging stressor. It is now generally accepted that prior exposure of a cell or tissue to a mild stressor can confer protection against a subsequent lethal stressor, and induction of stress proteins are involved (Mestril and Dillmann, 1995). This effect is known as pre-conditioning, and can be achieved by pre-exposure to the same type of stimulus (auto-protection), or by exposure to an unrelated stimulus (cross-protection).

Cross-Protection

The concept of cross-protection has been extensively studied in ischemia/reperfusion, a significant cell stress. Hyperthermia has been used as a means of protecting cardiomyocytes against ischemia-induced injury (Mestril et al., 1994). Studies have shown that a prior, hyperthermic treatment of animals can result in a significantly improved myocardial salvage following subsequent coronary artery occlusion and reperfusion in rats (Donnelly et al., 1992), and in an isolated, perfused rabbit heart model (Walker et al., 1993). The fact that cardiomyocytes respond to hypoxia (diminished oxygen levels) and metabolic stress with increased hsp70 production, points to a protective role for heat shock proteins during ischemia/reperfusion injury (Iwaki et al., 1993).

Currie and co-workers confirmed the protective role of hsp's. They found that isolated perfused hearts from rats which had received a 15 minute heat treatment at 42° C., 24 hours previously, exhibited an improved contractile recovery after a 30 minute period of low-flow ischemia followed by reperfusion as compared to hearts from non-heat treated animals (Currie et al., 1988). Obviously, whole body or whole organ heat stress results in many cellular changes (besides an increase in the expression of heat shock proteins) that could be responsible for the observed protection against ischemia. Nonetheless, recent studies have shown that the levels of hsp's and, in particular, the amount of hsp70 present, following whole body heat shock, are directly related to the degree of myocardial protection obtained (Hutter et al., 1994).

EM Fields, Hsp's and Cross-Protection

These findings, taken with evidence that induction of the heat shock response can protect against UV (Tyrrell, 1996) and X-ray (O-Rourke et al., 1997) damage suggest that heat shock protein responses may play a role in protection against various forms of oxidative stress. This is intriguing, given the discovery that short (20 minute) pre-exposures to 60 Hz magnetic fields could induce protection against anoxia/re-oxygenation in a chick embryo model (Di Carlo et al., 1998; Di Carlo et al., 1999). That work was based on earlier studies done by Blank et al. (1994) which showed that 60 Hz magnetic field exposures yielded the same patterns of protein synthesis as heat shock. Later studies confirmed this finding by demonstrating that fields activate heat shock factor (Goodman et al., 1994) and enhance transcription of hsp70 (Lin et al., 1997).

The induction of the hsp70 protein by a 60 Hz magnetic field exposure was found to be rapid, with maximum accumulation of the protein in as little as 40 minutes after exposure (Han et al., 1998). The same group also demonstrated that AP-1, AP-2, and SP-1, other stress-induced transcription factors were activated in response to EM field exposures. I have found that activation of HSF in chick embryos occurs within 10 minutes after the start of a 60 Hz, 8 micro Tesla ($\mu$T) EM field exposures. This strongly supports that the anoxia protection observed is caused by the field-enhanced activation of cellular stress responses similar to those seen during heat shock. This shows that EM field exposures induce responses similar to those caused by heat and other stressors, and has been discussed extensively in the aforesaid U.S. Pat. Nos. '685; '665; and '859.

EM Field Exposures Induce Protection Against a Number of Stressors

I discuss below studies and data (Table 1) that show that EM field exposures can induce protection against a variety of stressors. Tabular results are given as a ratio of survival seen in stimulus-exposed embryos as compared to survival in non-stimulus exposed controls (E/C ratio).

TABLE 1

Use of EM Fields and Other Stimuli to Enhance Protection Against Damage from Secondary Stressors

| First Stimulus | Secondary Stressor | E/C |
|---|---|---|
| 60 Hz EM Field | Hypoxia | 1.83 |
| 60 Hz EM Field | UV Light | 1.73 |
| 60 Hz EM Field | X-Rays | 2.20 |
| 915 MHz EM Field | Hypoxia | 1.61 |
| Heat Shock | Hypoxia | 1.54 |
| Heat Shock | High Dose X-Ray | 2.32 |
| Low Dose X-Ray | High Dose X-Ray | 1.88 |

EM Field Exposures Induce Hypoxia Protection

In accord with DiCarlo, et al., 1999, Chick embryos were exposed to a 60 Hz EM field for 20 minutes. Following exposure, embryos were rested for one hour and placed into hypoxia. Final mortality observations were made following re-oxygenation (Table 1). Exposure to a 60 Hz EM field induced statistically significant protection against hypoxia. To confirm that activation of the heat shock pathway would also yield protection, other embryos were heated at 43° C. and exposed to hypoxia as described above. Heating was protective, in agreement with my hypothesis that hsp's are part of the mechanism induced by the 60 Hz EM field.

Microwave Exposures Protect Against Hypoxia

I have discovered that microwave exposures (915 MHz) can also induce hypoxia protection in chick embryos (Table 1). This protection was statistically significant (P<0.01). The P value is the probability that two results (e.g., control survival and exposed survival) might be different by random chance. Traditionally, P values of less than 0.05 constitute a statistically significantly difference between two numbers.

EM Field Exposures Protect Against Ultraviolet Damage

As described by DiCarlo et al., 1999, chick embryos were exposed to 60 Hz, 8 $\mu$T EM fields for 20 minutes to determine if this could protect against damage from UV light. They were "rested" for 30 minutes prior to placement beneath a UV light source. Embryo survival was assessed one hour after UV (Table 1). EM field exposure induced significant protection (P<0.001) in the chick embryo against UV damage as compared with non-pre-exposed control embryos.

EM Field Exposures Protect Against X-Rays

Damage caused by x-rays is primarily due to the production of reactive oxygen species. Thus, I used heat shock, low-dose x-rays, and EM fields to induce protection in chick embryos against damage from subsequent high doses of x-ray irradiation (Table 1). Protection induced against high dose x-rays by each of 3 pre-conditioning stimuli is shown: heat shock; x-rays, and EM fields. For all stimuli, a significant increase in protection is induced (P<0.05). These data reaffirm the hypothesis that under certain conditions EM field exposures can protect against general oxidative stress.

TABLE 2

Hypoxia Protection Induced by EM Fields with Different On/Off Intervals (30 minutes total on time)

| On Time per Cycle (mins.) | Off Time per Cycle (mins.) | # of Cycles | E/C | P† |
|---|---|---|---|---|
| Control | Control | 0 | 1 | — |
| 30 | 0 | 1 | 2.08 | <0.001 |
| 5 | 1 | 6 | 1.68 | <0.016 |
| 5 | 2 | 6 | 1.45 | <0.06 |
| 10 | 5 | 3 | 1.61 | <0.031 |
| 10 | 10 | 3 | 1.73 | <0.027 |
| 10 | 15 | 3 | 1.90 | <0.016 |
| 10 | 20 | 3 | 1.65 | <0.018 |

In addition, I have discovered that in order to achieve protection with an EM field exposure, it is not necessary that the exposure time (a minimum of 20–30 minutes) be continuous. In other words, one must only be exposed to a cumulative dose of 20–30 minutes of total exposure time in order to obtain a protective response. For example, the thirty minutes of exposure might be given in three 10-minute, or six 5-minute exposures given over a period of 90 minutes. Data in support of this hypothesis is given in Table 2. Chick embryos were exposed to EM fields (60 Hz, 8 $\mu$T) for a total of 30 minutes of "on time". The only difference between the exposures used in Table 2 are the duration of the on time intervals (5 or 10 mins) and the duration of the off time intervals (1 or 2 mins off time for the 5 mins on time and 5, 10, 15, and 20 mins off time for the 10 mins on time). As can be seen in the table, significant protection is induced when the EM field is on continuously for 30 minutes (P<0.01). However, full protection can also be achieved even if the fields are turned off for as long as 2 minutes (for each 5 mins on time intervals) or 20 minutes (for each 10 mins on time intervals). This indicates that as long as the total on time of exposure is at least 30 minutes, the EM fields can be off for as long as 20 minutes at a time during the exposure period.

Other Clinical Applications of EM Field Exposures

The healing of non-union bone fractures with EM fields in humans and animals has been demonstrated (Fitzsimmons et al., 1986; McCleary et al., 1991), and the use of pulsed EM fields was approved by the Food and Drug Administration in 1979 for treatment of non-union bone fractures. EM Field exposures have also promoted accelerated wound healing (Dindar et al., 1993), and as a treatment for inflammation in wound healing (Detlavs et al., 1996).

The findings described above teach away from my discovery that EM fields can be used to sensitize biological cells and weaken the body's ability to respond to stresses. I have discovered that appropriate EM fields can weaken the stress response of cells, and can be used to increase the efficacy of x-ray and other cancer treatments and for alleviating the effects of auto-immune diseases.

EM Fields and X-Rays

There has been previous art describing possible interactions of EM fields and x-ray exposures in several systems. Nearly all of these studies, however, were conducted to determine if the synergistic application of EM field and x-rays would lead to an increased incidence in cancer. This is in contrast to my discovery that adjuvant therapies utilizing the combination of EM field and x-ray will enhance the killing of cancer cells, not cause their initiation. Given the controversy surrounding a possible role for EM fields in the etiology of developing cancers, researchers sought to determine if EM fields alone, or if used in conjunction with other known carcinogens such as x-ray exposures, could increase the probability of the development of tumors. In the prior art experiments described below, x-ray exposures were used to initiate the cancer, and the EM field exposures were shown to be co-promotion agents. This teaches away from my discovery that EM fields can be used as anti-cancer agents.

In 1993, Svedenstal and Holmberg looked at lymphoma development in mice exposed to x-rays and pulsed magnetic fields. The x-rays were used to initiate cancer development. EM fields were applied to the animals to see if there was an increased incidence of lymphoma. Their findings indicated several correlations between the ability of x-rays to induce lymphomas in the presence and absence of an EM field. This teaches away from my discovery that EM fields under certain exposure conditions can be used to help inhibit cancers. In similar studies, Myakoshi et al. (1999) and Walleczek et al. (1999) saw that exposure of Chinese hamster ovary cells to EM fields coincident with x-ray irradiation led to an enhanced rate of mutation as compared to cells exposed only to the x-ray. Again, these studies imply that EM fields can actually help cancers to grow, not assist in their destruction as has been my discovery. In addition, the EM field exposures used in the Myakoshi study were applied for more than 40 days, and both experiments used EM field applications that were simultaneous with or following the x-ray exposure. These findings teach away from my discovery that EM fields can inhibit tumor growth when applied prior to and in conjunction with x-ray radiation.

EM Fields and Chemotherapeutic Agents

Research covering a broad range of treatment chemicals (Chang et al., 1980; Omote et al., 1990; Cadossi et al., 1991, Pasquinelli et al., 1993; and Salvatore et al., 1994) has suggested that the efficacy of chemotherapy drugs used to treat cancer can be modified by exposure to an EM field. In these studies, comprising mouse in situ tumors, MCF-7 breast cancer, leukemic and chemo-resistant cell lines, EM fields were applied after application of the chemotherapeutic agent This teaches away from my invention, which demonstrates that EM field exposures will be maximally effective in increasing cell death from chemotherapeutics when applied prior to application of the anti-cancer agent. In addition, in several of the studies (Omote and Chang), the strength of the magnetic field used was up to 100 times higher than those utilized in my discovery, and the signals used were a very special pulsed field (Cadossi and Pasquinelli) which induced electric fields 1000 times higher than those which I have found effective. The practicality of their findings is severely limited by the necessity to use very long (at least 96 hours), continuous exposures to high magnetic fields (on the order of 1 Gauss). These requirements, therefore, render their exposure protocols clinically and commercially impractical. This is in contrast to my discovery that the EM fields will have their maximum effectiveness when applied prior to application of the chemotherapeutic drug. This, I have discovered, is because the EM field exposures down-regulate the levels of heat shock proteins within the tumor cells, rendering them more susceptible to the chemotherapeutic agent. For greater anti-tumor effects the EM field can be applied both prior to and for several days following application of anti-cancer agents such as ionizing radiation and toxic drugs. However in all cases the most important exposure is that which occurs prior to chemotherapy or x-radiation.

REVIEW OF TREATMENT INVENTIONS

I have discovered the following concepts: It is possible to use EM fields to induce protection against various forms of stress. The protection that is induced, however, is highly dependent on the dose of the EM field used. Short-term field exposures (ranging from 20 minutes to several hours) are protective against stress and can also reduce cytokine expression which leads to swelling and inflammation.

I have also discovered that long-term prior exposures (greater than 12 hours) can cause cells, tissues and organs to be more susceptible to subsequent damage from stress. The degree of protection or increased susceptibility depends upon the time duration of exposure and the strength of the applied EM field. Table 1 gives data which demonstrates how the duration of exposure can dramatically affect hypoxia, UV light and x-ray protection induced by EM fields. Chick embryos were exposed to 60 Hz, 8 $\mu$T EM fields 1, 8, 10, 24, 48 or 96 hours, immediately prior to hypoxia or WV light. Mortality measurements were taken after the end of hypoxia, UV light or x-ray stress. Data is expressed as the ratio of survival in the exposed embryos compared to survival in the non-EM field-exposed embryos (E/C ratio).

TABLE 3

Use of EM Fields to Alter Protection Against Hypoxia UV Light and X-Ray Stress

| Duration | Hypoxia Stress | | Ultraviolet Light Stress | | X-Ray Stress | |
|---|---|---|---|---|---|---|
| | E/C | P† | EC | P† | E/C | P† |
| 20 minutes | 1.78 | <0.001 | 1.62 | <0.001 | 2.16 | <0.001 |
| 1 hour | 1.8 | <0.001 | *** | *** | *** | *** |
| 8 hours | 1.83 | <0.001 | *** | *** | *** | *** |
| 10 hours | 1.42 | <0.01 | *** | *** | *** | *** |
| 24 hours | *** | *** | 1.36 | <0.05 | *** | *** |
| 48 hours | *** | *** | 0.91 | 0.652 | *** | *** |
| 96 hours | 0.7 | <0.01 | 0.71 | <0.01 | 0.45 | <0.01 |

***measurement not taken

All time durations of exposure, except for 96 hours, yielded significant increases in hypoxia protection. Following 96 hours of EM field exposure, however, a significant decrease in hypoxia protection was noted. For example, as can be seen in Table 3, the maximum protection against hypoxia stress is observed between 1 to 8 hours of exposure time. At times less than 1 or greater than 8 hours (up to 12 hours), hypoxia protection is still observed, however to a lesser extent.

With long-term EM field exposures prior to UV light stress, maximum increased susceptibility occurs at times greater than 48 hours, although some increased sensitivity and susceptibility is noted at times between 12 and 48 hours. Similar results can be obtained using EM fields up to frequencies as high as several GHz and at intensities of the order of several milliwatts/cm$^2$ and higher. The table shown here clearly demonstrate that the dose of EM fields used is critical in predicting their effect. It is important to note that none of the fields I have used cause a measurable rise in the temperature of the tissue.

Significant UV protection is seen only for the 20 minute and 24 hour exposure, with significant de-protection observed for the 48 and 96 hour time points. This led me to hypothesize that EM fields could also down-regulate protection against x-rays, another significant contributor to oxidative stress.

Table 3 shows how survival after x-ray irradiation of 96 hour EM field-exposed embryos compares to embryos not exposed to EM fields. I have discovered that when chick embryos are exposed to a 60 Hz, 8 µT EM field for 96 hours, the percent survival is decreased x-ray exposure. My discovery that EM fields of varying frequencies and time duration can reduce the stress response capabilities of cells led to the therapeutic applications I have found and described below.

I have also discovered that long-term, continuous microwave exposures, (e.g. 915 MHz) can down-regulate protection against subsequent anoxic stress. Embryos were exposed to microwaves for the last final 48 hours of their incubation. Following administration of anoxia and re-oxygenation, embryos were evaluated to determine mortality. I found that those embryos that had been exposed to the microwave were less capable to deal with the insult from the subsequent anoxia (data not shown).

In addition to the ability of long-term EM field exposures (on the order of 48 to 96 hours of exposure time) to down-regulate the protective heat shock response, I have also discovered that short-term field exposures, if repetitive over a period of several days, can accomplish the same type of down-regulation and decrease protection against insult. This exposure protocol is extremely important for commercial and clinical feasibility of the use of EM fields to treat disease. In a series of 3 separate studies, chick embryos were exposed to different EM field exposure intervals over a period of four days. All 60 Hz EM exposures were done at 10 µT. At the end of the four days of incubation, embryos were subjected to hypoxic stress. Final observations of survival of control and exposed embryos were made following the end of hypoxia. Data is shown in Table 4.

TABLE 4

Repeated Exposure to EM Fields Decrease Protection Against Damage from Hypoxia Stress

| Time Duration of Exposure (over 4 days) | E/C | P† |
|---|---|---|
| 1 hour twice daily | 0.65 | <0.008 |
| 30 minutes twice daily | 0.52 | <0.017 |
| 30 minutes once daily | 0.69 | <0.08 |

As can be seen in the table, all three exposure regimens were effective in lowering the hypoxia protection of those embryos which had been exposed to the EM fields (E/C ratios less than 1 indicate a decreased survival in EM-exposed embryos as compared to controls). The greatest percent decrease in protection was noted for the 30 minutes, twice daily exposure condition (48%). The other regimens showed an approximate 34% decrease in hypoxia protection as compared to sham-exposed controls. Clearly, the repetitive nature of the EM field exposures are somehow decreasing the ability of the embryos to protect themselves against the potentially-lethal hypoxic stress. Similar patterns of decreased hypoxia protection are observed when EM field exposures are maintained continuously throughout the 4 day incubation period.

In considering the results presented in Tables 2 and 4 above, it will be seen that 30 minute exposures given each day over a period of several days will down-regulate protection against hypoxia even if the 30 minute exposures are not continuous. I have discovered that down regulation still occurs if cumulative 30 minute exposures are given repeatedly, once or twice daily over a period of several days. By cumulative I mean that even if the exposures are interrupted for several (e.g. up to 20) minutes they still induce down regulation if given repeatedly over several days. I also have discovered that the continued exposure once daily to the EM field after the stress treatment will continue to enhance effectiveness.

My inventions should be very useful in chemotherapy. The application of my special electromagnetic fields to tumor cells will make them more susceptible to subsequent treatments using toxic chemicals. For example, taxol is used in chemotherapy because it hinders the growth process of tumor cells. I have investigated the effect of EM fields on the ability of taxol to create abnormalities in rapidly dividing cells. The model for this purpose was chick embryos. The embryos were incubated in the presence of a 60 Hz, 8 µT EM field. After 48 hours of continuous incubation, either dimethyl sulfoxide (DMSO) alone (controls) or Taxol dissolved in DMSO was injected. EM field incubation was continued for an additional 48 hours. At the end of 4 days incubation, embryos were visualized and classified as normal or abnormal (deformed, young, or dead). The results are shown in Table 5.

TABLE 5

Effect of EM Field Exposures on Taxol-Induced Abnormalities in Chick Embryos

| Treatment | Percent Abnormal Embryos |
|---|---|
| Taxol Alone | 19.3 |
| Taxol + EM Fields | 31.1 |

It can be seen from Table 5 that the exposure to EM fields beginning prior to introduction of the taxol incubation of embryos with taxol in an EM field leads to a very significant increase in the toxic effect of the taxol. Although in this example the EM field stays on after the taxol has been injected I have found that similar effects can be obtained even if the field is turned off prior to administration of the taxol. Thus, I have discovered that long-term exposure to EM fields can lead to a down-regulation of the biological cell's ability to respond to, and thereby protect against a chemotherapeutic agent. This increase in sensitivity to toxic agents can be achieved with fields ranging in frequency from as low as 30 Hz to as high as 1 GHz. The type of field to be used will be determined by cost of equipment and ease of application.

It will be obvious to a person skilled in the art upon reading this application that this technique could be applied to other medical procedures using deleterious stimuli which are intended to destroy or modify a chosen volume of tissue or biological cells for a reason other than cancer therapy. Some examples of this are benign growths, keloids, arteriovenous malformations, benign prostatic hyperplasia, splenomegaly, etc. Further, the adjuvant application of this technique is not only for treatment intended to cure, but could also be to aid in palliative measures, for example, with ionizing radiation used for reducing the mass or growth of a tumor to temporarily relieve symptoms caused by that mass.

In regard to auto-immune diseases, these are difficult to treat and cure because they turn the body's immune system against its own tissues. The primary defenders in the immune response are the cytotoxic T cells and the antibody-secreting B cells. T cells are "programmed" to destroy any cells showing abnormal proteins on their surface. For the purposes here, abnormal refers to any protein that is not normally displayed on the cell. They are also targeted to objects coated with antibodies. In autoimmune diseases, B cells make antibodies, which erroneously attach to self tissues and trigger their destruction by the T cells. Surface expression of stress proteins (normally found only in the interior of cells) has also been linked to the autoimmune diseases detailed below. Studies have shown that only diseased cells, not normal cells, can be made to express stress proteins on their cell surfaces. Both heating and treatment with toxic chemicals have been shown to cause this phenomenon. This is of significance, because heat shock proteins have been shown to function as immune modulators, providing a target for cytotoxic T cells. When the T cells detect a cell with stress proteins on the surface, they are then activated to destroy the cell even when the cell is normally functioning and much needed.

I have found that I can control this immune over-response through the use of specific EM field exposures. I can down-regulate the heat shock protein response with repeated exposures to EM fields, leading to a decreased surface expression of heat shock proteins, and a lowered immune response against the abnormal surface marker. This down regulation will slow the progress of the autoimmune disease, and/or minimize the discomfort. In each of the autoimmune diseases described below, it is obvious to someone skilled in the art that the unwanted appearance of surface stress proteins is a factor both in the progression of and the pain and discomfort caused by the disease. For the adjuvant use of EM fields with anti-cancer therapies as well as in minimizing discomfort from auto-immune diseases, down-regulation of the heat shock responses is the method of choice.

A typical application using an EM field to down-regulate stress proteins in patients suffering from auto-immune disease would be the following. Apply a low frequency EM field (from 20 Hz to 60 kHz) whose field strength is above 20 $\mu$T. For down-regulating the stress response, the EM field exposure should given as repeated exposures (for optimal effect, at least 1 hour, twice daily (at a minimum of 10 hour interval between the two exposures on any given day). These twice daily exposures should be done throughout treatment. If this exposure protocol is not practical for a given patient, exposures may also be done for 30 minutes twice daily or 30 minutes once daily, since both of these treatment protocols will also be effective. At the very least, there must be at least 30 minutes of cumulative EM field exposure time (over a period of several hours). If the EM field is in the radio frequency range the applied radiation energy density should be greater than several milliwatts per square cm.

In the case of Multiple Sclerosis (MS), this disease is characterized by deterioration of the myelin surrounding nerves. Myelin is composed of the fatty membrane of cells, which wrap around the nerves. These cells are called Schwann cells. The loss of myelin can cause symptoms such as fatigue, and gait difficulties. There is no known cure for this disease. However, it is possible to slow it progression and minimize symptoms. Current measures include modest exercise, and avoidance of hot climates and stressful life events. This is because one of the major targets in MS is stress proteins. The immune system destroys the myelin of nerve cells expressing stress proteins, leading to increased severity of symptoms (Birnbaum et al., 1997). In addition, altered expression of hsp70 has been found in the lesions and myelin of MS patients (Aquino et al., 1997). Symptoms of MS are intensified after increases in body temperature from a bath, or over-exertion. Exercise is important to maintain muscle strength, but the expression of hsps can make MS worse, by providing a marker for autoimmune attack. In some cases, the drug Avonex can alter aspects of the immune system, suppressing the destruction of myelin. This therapy, however, can cost up to $10,000 annually.

Another treatment that is currently in clinical trials and shows some promise is the administration of taxol (the same drug used in chemotherapeutic applications). The therapy is administered once a month, and has been shown to lower the severity of symptoms associated with MS. The extended presence of Taxol in the tissues down-regulates the stress protein response. A lowered response means that stressors will not induce the expression of hsp on the surface of the Schwann cells, and an immune "over-response" will be avoided. The end result will be a decreased inflammatory response of the immune system. This translates into fewer attacks on the myelin, and will lead to a decrease in disease symptoms.

The Taxol treatment, however, is risky, in that any time a drug, especially a chemotherapeutic agent, is introduced into the body, there is the possibility of serious side effects. I have discovered that EM field exposures can be used to down-regulate the hsp response without causing additional damage, leading to the same lowered immune response. Specifically, these non-invasive EM field exposures, could also be used to lower the expression of hsp on the surface of the myclin-producing Schwann cells. This treatment will then permit the patient to partake in exercise without triggering increased severity of symptoms. The EM field treatment can be used in conjunction with drugs used to treat auto-immune disease, in order to increase their efficacy, thus allowing for lower doses of drugs, and a consequent reduction of side effects.

Arthritis is characterized by pain, swelling, stiffness, and often disabling joint inflammation. In rheumatoid arthritis, the most severe type of inflammatory joint disease, the body's immune system acts against and damages joints and surrounding soft tissue. Evidence suggests that this targeting of the synovial cells and fluid is triggered by an auto-immune reaction due to the presence of stress proteins in the joint (Schett et al, 1998). When the joint is being manipulated, as during exercise, there is a mechanical shearing stress imposed on the cells and tissue within. This mechanical stress can lead to the induction of the stress protein response through the release of inflammatory cytokines by the damaged cells, and possibly the expression of these stress proteins on the cell surface. In the case of rheumatoid arthritis, it is believed that the immune cells of the body detect the abnormal surface expression of stress proteins and mount an overblown protective response. The accumulation of cells and fluids relating to the immune response is what leads to the pain and swelling associated with the disease. There is no cure for most types of arthritis. However, many forms of arthritis respond to a wide range of alternative therapies. I have discovered that by using the EM field exposures described in this application, it is possible to down-regulate stress protein levels on the cell surface, thereby limiting the immune response against synovial tissues and leading to decreased swelling of the joint. This, in turn, will increase mobility, and lessen pain.

Diabetes mellitus is a group of diseases characterized by high levels of blood glucose resulting from defects in secretion and/or action of insulin, a protein responsible for enhancing the uptake of consumed sugars into cells. Diabetes can be associated with serious complications and premature death. People suffering from this disease must receive insulin from external sources in order to maintain a reasonable lifestyle. Insulin-dependent diabetes has recently been linked to stress proteins, and heat shock proteins have been suggested as the primary antigens. In fact, a current experimental drug therapy, Bimoclomal, has been shown to affect the stress protein response (Szigeti et al., 2000), and has shown promise as a potential clinical tool. In certain forms of diabetes, the presence of the stress proteins on the cell surface of the pancreatic islet cells (which secrete insulin) leads to their destruction via an auto-immune reaction. Surface expression of stress proteins has been shown to enhance removal of the pancreatic cells by the immune system, by providing a target for the cytotoxic T cell response. I have discovered that long-term EM field exposure therapy can down-regulate the stress protein response in the diseased cells. Because the loss of these cells from the over-active immune response is a progressive condition, lowering of the islet cell surface expression of hsps can lead to reduced destruction. With more cells available to produce insulin, the diabetes will be less severe and its progression will be slowed.

The disease known as psoriasis is characterized by scaly red patches, or eruptions of the skin. Auto-immune processes have been suggested as playing a pathogenic role. Psoriasis is believed to occur because T cells trigger an abnormal inflammatory response in the skin tissue. Since immune responses to infections are often directed towards hsp's, studies were initiated which showed that the skin cells of individuals with psoriasis express higher-than-normal levels of hsp's (Boehncke et al., 1994). Thus, the expression of heat shock proteins by skin cells has been postulated to be a significant factor in the physio-pathology of psoriasis. This is not unexpected, given that outbreaks can be exacerbated by exposure to stressful life events and heat. Taxol injections, as discussed above, have also been shown to minimize inflammation. In addition, a current treatment for psoriasis involves the once daily topical application of tazarotene, (a retinoid derivative of Vitamin A). Prolonged exposure to retinoids (given daily) has been shown to down-regulate expression of hsp70 (Tosi et al., 1997). This is consistent with my invention using EM field exposure, which also works by down-regulating expression of hsp70, to minimize the inflammation and over-immune response associated with psoriasis, either alone, or in combination with existing therapies.

OPERABILITY OF INVENTIONS

Operability is based on two principles:

1. Ability to selectively either protect or de-protect a volume of tissue depending on the parameters of the EM field exposure applied; and 2. Ability to selectively target specific volumes of tissue (i.e. focusing the effect of the field) with chosen EM field exposures to elicit the desired biological effect.

These applications are aided by methods separately used in applying cancer therapeutic agents, which facilitate targeting these agents to a treatment volume or to cancerous cells (for example the focusing of ionizing radiation used in conjunction with the EM field exposure).

Application of EM fields activates cell signaling pathways resulting in the production of stress proteins. These stress proteins protect the cell against deleterious stimuli. However, I have discovered that prolonged or repetitive stimulation causes the cells to diminish or down-regulate this stress response. This leaves the cells in a more sensitive state after EM field exposure. Therefore, any therapeutic agent applied to damage these cells will be more effective.

The working hypothesis for the mechanisms presented is not intended to be limiting. There may be additional or different mechanisms of action not yet recognized which are related to the change in sensitivity of a biological cell exposed to EM fields. There may even be some cellular mechanisms that work in contrast to the overall effect being targeted. The effect being targeted is the net biological change in cellular sensitivity to a given therapy. (Borrelli et al, 1996; Fuks et al., 1994; Kang et al., 1998; Matsumoto et al., 1998; Ruiter et al., 1999; Strasser and Anderson, 1995; Trautinger et al., 1997; Watters, 1999; Walter et al, 1997; Xu et al., 1998).

An Example Using Radiation Therapy (RT):

This example uses Radiation Therapy (RT), but when properly modified for the particular application, applies equally well to other forms of cancer therapies. These include, but are not limited to chemotherapy, hyperthermia, tissue ablation, photo-dynamic therapy, non-thermal ultrasound therapies, gene therapy, etc.

An EM field is applied to a specific volume of tumor target tissue to sensitize the cells, for example, to cause a down-regulation in the ability to produce stress proteins within the cells. One of the proteins down regulated is the inducible form of hsp70 (hsp72). This is very important in mediating apoptotic cell death after deleterious stress (e.g. radiation) to cells. A decreased ability to induce hsp72 within the cell increases the probability the cell will undergo apoptosis in response to a particular dose of radiation. Apoptosis is thought to be the predominant form of cell death in radiation-dependent tumor regression. Therefore, down-regulating, or decreasing hsp72 in the target volume of cells by application of the proper EM field will increase the probability that the cells will die from apoptosis for a given dose of radiation. Other forms of radiation-induced damage resulting in reduction of clonogenic cells within a tumor volume will be similarly affected. (Gordon et al., 1997; He and Fox, 1997; McMillan et al., 1998; Samali and Cotter, 1996).

Summary of Treatment Inventions

To summarize at this point, my inventions involved with treatments using EM field exposures embrace a method of targeting and enhancing therapeutic or palliative treatments including, without limitation, physical, chemical, radiative or gene therapies applied for the treatment and prevention of diseases. An example of the disease is cancer, in which case the EM field treatment may be administered prior to treatment with anti-cancer agents. Also, the treatment may be applied to any autoimmune dysfunction, in which cane the EM exposures are best done at least 5 days per week (preferably 7), with each exposure duration lasting a minimum of 20 minutes (preferably 1 hour). Also embraced is an EM field treatment which is administered both prior to and following treatment with anti-cancer agents. In an exemplary case of the latter, the EM field exposures are administered over a period of a minimum of 2 days both prior to and following treatment with anti-cancer agents, with a minimum of 1 exposure each day, and preferably 4 days, and with each exposure duration lasting a minimum of 20 minutes, and preferably 1 hour.

DESCRIPTION OF PREFERRED EMBODIMENTS OF APPARATUS

Specific apparatus will now be described for applying appropriate, biologically effective EM fields to a chosen volume of tissue.

To aid in these descriptions, several drawings are made part of this application. A brief description of each is now given:

FIG. 1. Effects of on/off 60 Hz EM fields on hypoxia protection in chick embryos FIG. 2. Superposition of EM fields from two coils of equal amplitudes FIG. 3. Superposition of EM fields from two coils of unequal amplitudes FIG. 4. EM fields of Helmholtz coils and a single coil FIG. 5. Focusing effect of two alternately pulsing EM fields FIG. 6. Broader focus region from two alternately pulsing EM fields FIG. 7. General instrumentation, Example 1

FIG. 8. General instrumentation, Example 2

FIG. 9. General instrumentation, Example 3

FIG. 10. General instrumentation, Example 4

Figure 11:
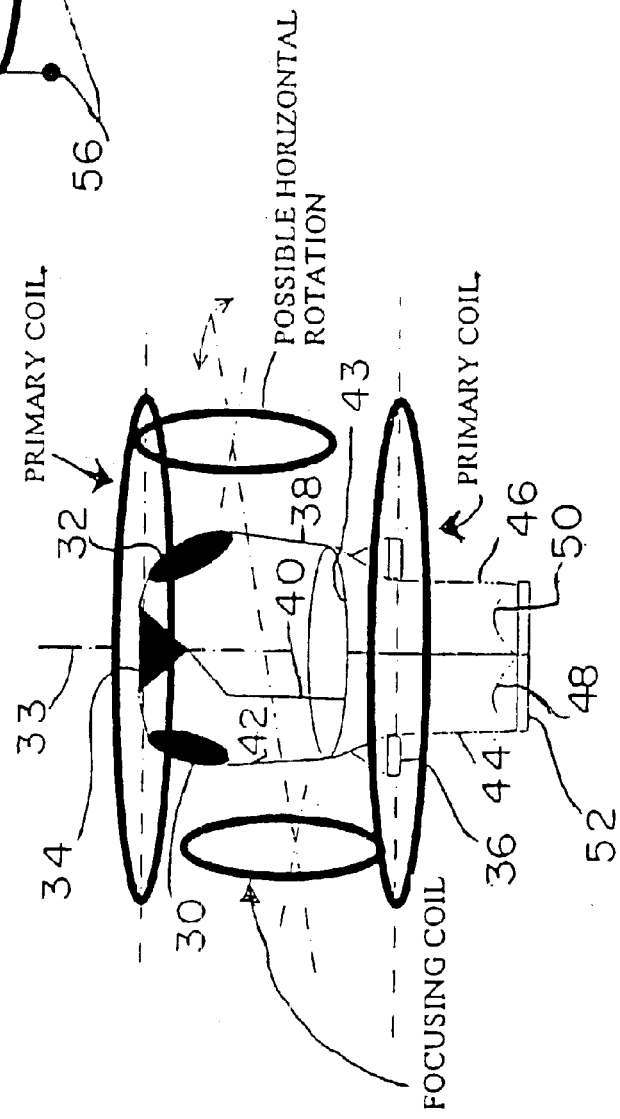

FIG. 11. Complex device, Example 1

FIG. 12. Complex device, Example 2

FIG. 13. Complex device, Example 3

Figure 14:
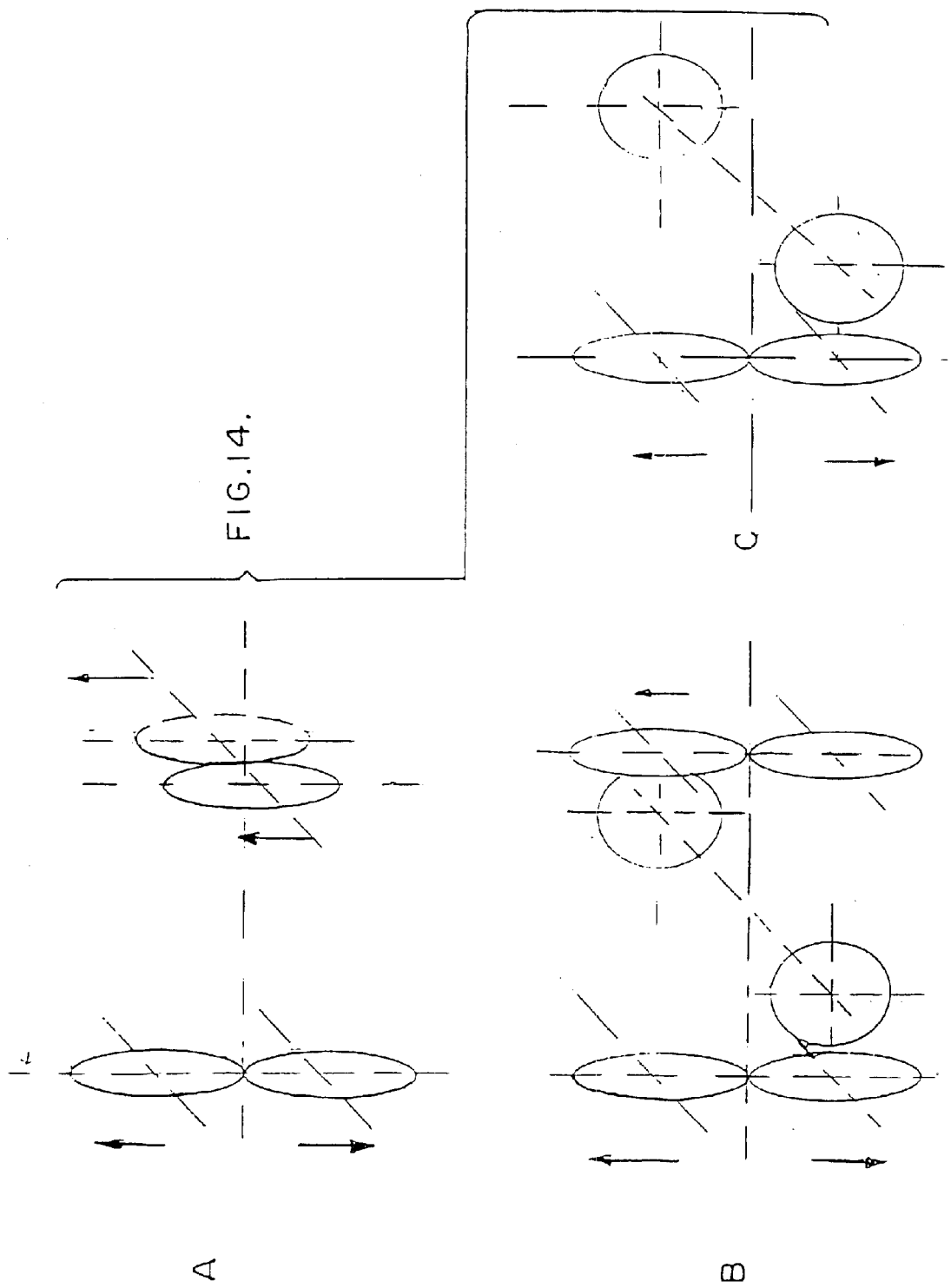

FIG. 14. Complex device, Example 4

FIG. 15. Complex device, Example 5

Figure 16:
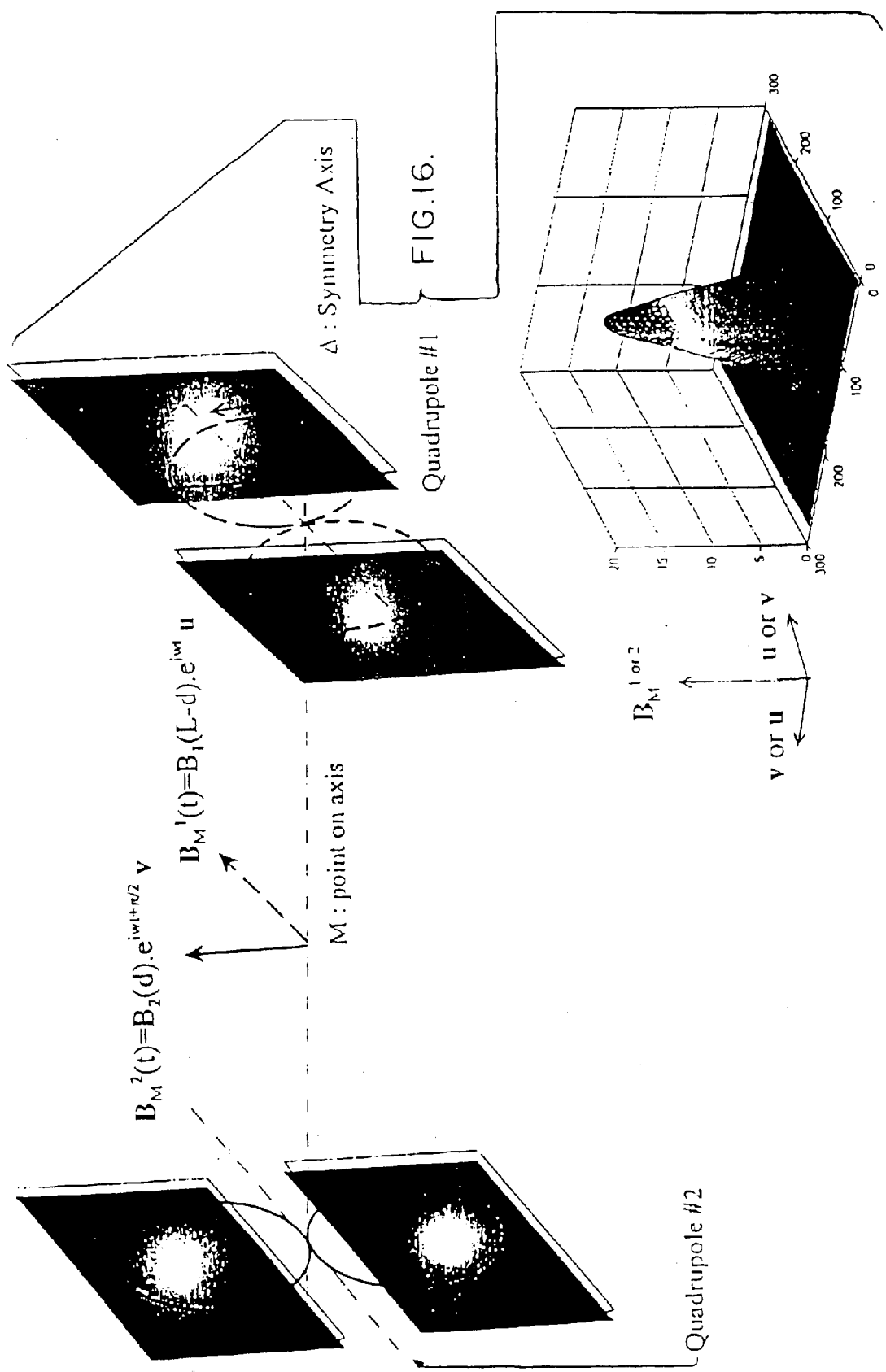

FIG. 16. Quadrupole, Example 1

Figure 17:
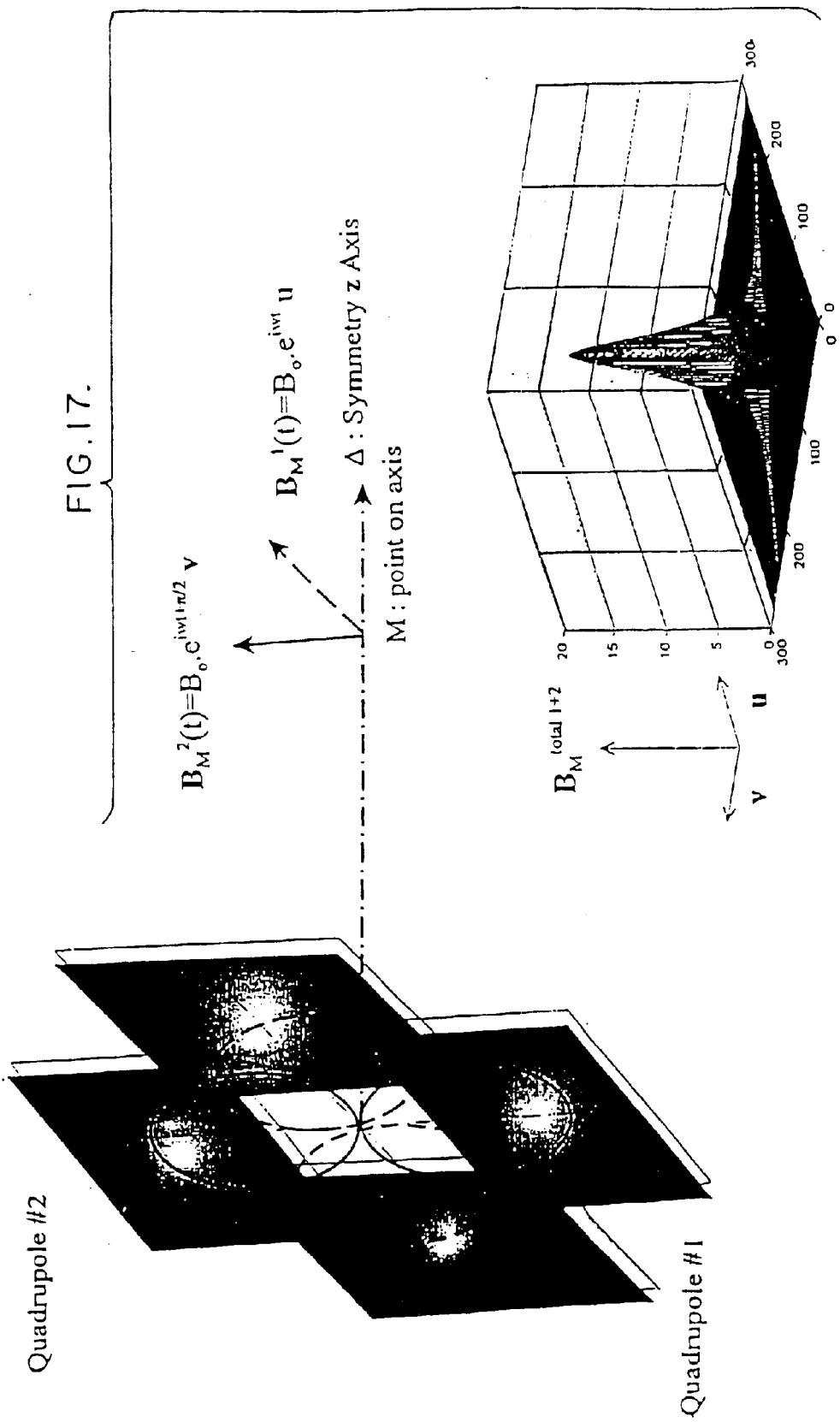

FIG. 17. Quadrupole, Example 2

Figure 18:
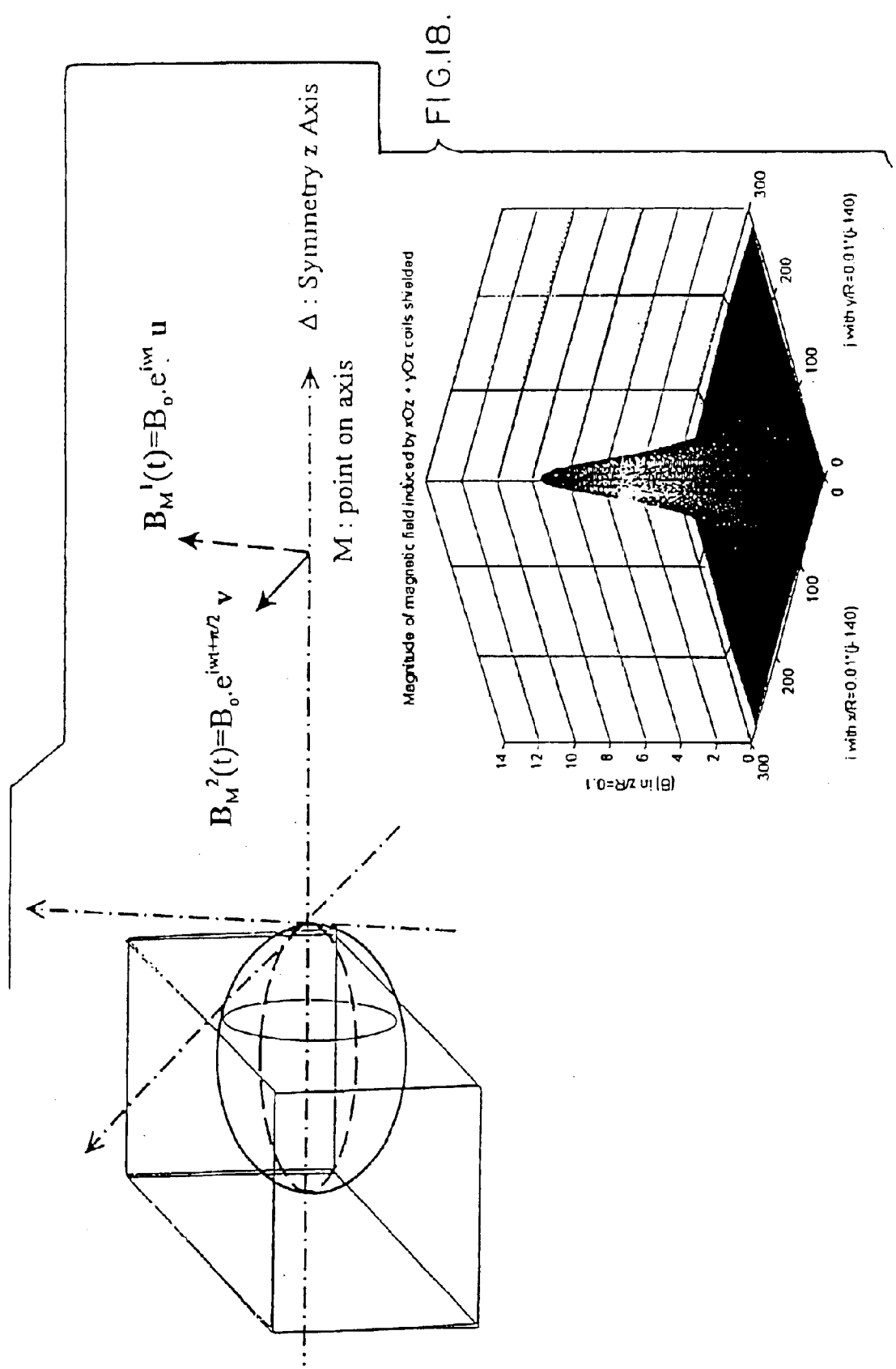

FIG. 18. Quadrupole, Example 3

For external application, single or multiple coils of conducting wire connected to a current source can be used to produce EM fields of desired magnitude, size, shape and location, at desired times, within the human or animal body. A power source and antenna can be used to direct the EM field to tissue volumes within the body.

To create a uniform EM field, a pair of circular coils can be placed outside the body in what is known as the Helmholtz arrangement. The planes of the coils are parallel to each other and separated by a distance which is approximately equal to the radius of the coils. This uniform arrangement can be used to treat large volumes of tissue. For example, using the field focusing technique described below a small region of tissue (e.g. a tumor) can be exposed for the length of time necessary to down regulate the stress response. Then prior to the application of a deleterious agent such as x-rays a larger region of tissue can be up regulated (i.e. enhanced stress proteins levels) by much shorter or lower doses of a non-ionizing EM field exposure. In this way the non-tumor region can be protected against any stray ionizing radiation.

Focusing of EM Fields to Specific Tissue Volumes

In the embodiments of the inventions described herein, methods are used which are more general and flexible as they pertain to a wide range of therapeutic applications, by either catalyzing or inhibiting the response of the cellular defense mechanisms towards the destruction of diseased areas or the protection of other areas against self-destruction. The present methods utilize a new approach to optimizing the frequency domain of the electromagnetic fields. They involve limiting the time exposure of the patient, preferably to less than 30 min a session, and also the amplitude of the fields, preferably less than 2000 $\mu$T. Furthermore, the present instrumentation design proposed to apply these low amplitude fields allows for focusing of the adjuvant effect on the diseased cells, tissues or organs, with a negligible or non-existing adjuvant effect on normal cells, tissues or organs.

Focusing the Bio-Effect of EM Fields

Variations of suitable apparatus for focusing EM fields will come to mind to persons skilled in the art. However, it is very difficult to focus a low frequency EM field down to regions of less than 1 cm cubed. This is particularly true if the tissue region is not near the surface of the body. To solve this problem I have invented and now describe a method for focusing the biological effect (bio-effect) of an EM field even when the EM field itself is not focused. It is based upon my discovery that an athermal EM field (i.e. one which causes no increase in tissue temperature) can cause significant biological effects (e.g. modification of heat shock protein concentrations) only if the field parameters (e.g. amplitude, frequency, waveform) are constant for periods of at least several seconds. (See FIG. 1 and Litovitz U.S. Pat. No 5,968,527). For example if a constant amplitude athermal EM field (that is normally bio-effective) is turned on and off at one second intervals it will have no biological effect. For significant bio-effect to occur the field would have to be turned on and off at intervals of at least several seconds, preferably at intervals of greater than 10 seconds (FIG. 1). See also the aforesaid U.S. Pat. Nos. '859, '665, and '685.

Thus, an athermal EM field applied to tissue which has on-off cycles ranging from approximately 0.1 second to approximately 1 to 2 seconds will have no biological effect. This EM field will have no effect on the heat shock protein activity (or any other protein) in tissue. By the same reasoning, an athermal EM field applied to a tissue which has on-off cycles of greater than 10 seconds will yield a full biological effect. In addition, I have discovered that if one superposes equal fields from 2 sources each being turned on and off at, for example, 1 second intervals (which would normally not yield a biological effect) and if the on time for one source is the off time for the other source (FIG. 2), then the sum field will be bio-effective. The cell "sees" this sum field as a constant field. I have found that even if the fields are not in the same direction a bioeffect will be induced. I have found that effects occur even if the field direction differs by up to 90 degrees.

If the amplitude of one of the alternating fields is smaller than the other (FIG. 3) then a diminished bio-effect occurs. The magnitude of the effect decreases linearly as the amplitude of the smaller field decreases. If the smaller field amplitude is below 50% of the larger field, the biological effect goes to zero. I have further discovered that the induced bio-effect is down about 50% when the amplitude of the smaller field is about 75% of the larger field.

I have discovered that when tissue is exposed to an on/off uniform field superimposed on an off/on (i.e. on when the uniform field is off) non-uniform field (i.e., a field which varies in space) there is a limited region of tissue where the superimposed fields are bio-effective. This bio-effective region is the region in which the two fields are approximately equal in amplitude, i.e., the fields are within 25% of each other.

One embodiment of this focusing invention is to; a) make a Helmholtz configuration by placing one of the Helmholtz coils on the front and the other on the back of the body and b) to place a single smaller coil within and approximately in the plane of one of the Helmholtz coils. The Helmholtz coil pair will create a uniform field that is turned on and off every second. The single coil is also turned on and off every second (off when the Helmholtz coils are on). Thus, the single coil will create a field which decreases with the distance from it as shown in the solid line curve in FIG. 4. The single coil should have sufficient number of turns and current flowing through it to create a greater magnetic field in the plane of the Helmholtz coil than that caused by the current through the Helmholtz coil itself. At some point the amplitude of the uniform Helmholtz field (shown as dotted and dashed lines in FIG. 4) and the non-uniform field due to the single coil will be roughly the same. At a distance further in to the body the field due to the small single coil will be less than that of the uniform field (See FIG. 4). By controlling the position of the single coil within the plane of the Helmholtz coil and the current in either the single or double coil configuration the position within the body where the two fields are approximately equal can be controlled. This can be seen in FIG. 6 where a low Helmholtz field (10 $\mu$T) matches the single coil field at around 13 cm into the tissue whereas a higher Helmholtz field (20 $\mu$T) matches the single coil field at about 9.5 cm into the tissue. I emphasize again each of these fields is on and off approximately every second, one being on when the other is off. The exact times that the coils are on and off are not critical as long as the time lies in the range preferably from 0.1 to 2 seconds. In addition, when the peak fields of the two coils are equal in a given region of tissue, the sum of the two fields must be reasonably constant in time. This constancy requirement includes constancy of all field parameters including frequency, waveform, and amplitude.

To be bio-effective, the percentage decrease from the larger to smaller field must be significantly less than 50%. The bio-effectiveness of a fluctuating signal as pictured in FIG. 3, decreases linearly as the smaller signal falls to lower values. When the smaller signal is approximately 50% of the larger, the bio-effectiveness is zero. In practice the EM induced bioeffect significantly decreases the resistance of a cell to deleterious stimuli when 1) the cell is exposed to the combined field for a period greater than 48 hours and the lower field is greater than approximately 70% of the larger field throughout the duration of the exposure. The EM field exposure during this time period need not be constant, but must be repeated either once or twice a day for a periods of about 30 minutes or more.

The results of the concepts described above are exemplified in FIG. 5. Here the bioeffect of an EM field is focused about 9.5±1 cm into the body. The exposure conditions described here are as follows. The single coil is 5 cm in radius. The number of turns and the current in it are such that the single coil field is equal to 20 $\mu$T at a distance of about 10 cm into the tissue. The Helmholtz field is 20 $\mu$T (the higher peak Helmholtz field in FIG. 2).

If it is desired to broaden the bioeffective focus region, this can be done in a number of ways. For example any arrangement which causes the spatially varying field to decrease less rapidly will broaden the region in which the uniform and non-uniform fields will be reasonably close in amplitude. Upon reading this application, any one skilled in the art can think of many ways to arrange coil systems to do this. One method for example is to place small coils in the planes of both Helmholtz coils. These small coils should have their fields opposing each other. The resulting field between these two small coils would drop faster than that of the single small coil described above. Of course the pulsing field of the small coils is, as described above, on when the pulsing field of the Helmholtz coils is off.

I also have discovered a more flexible way of controlling the size of the bioeffective focus region. The method is based upon the fact that if a field is on for times greater than 10 seconds and then off for an approximately equal time or less it still induces a bio-effect (FIG. 1). If, for example, one now causes the amplitude of the current in the Helmholtz coils (that are coming on and off every second) to alternate between two values every 20 seconds, then the peak field of the Helmholtz coils will alternate between two values every 20 seconds. In this case, the region where the Helmholtz field is close in value to the single coil field will alternate between two points in the tissue. Since each region sees a relatively constant field for 20 second periods, each region will have bioeffects induced (i.e. stress protein production will be affected). In FIG. 6, I have plotted the superposition of the effects of the field values of the Helmholtz coils. In this figure the peak field of the 1 second duration pulses of a 60 Hz Em field caused by the Helmholtz coil varies from 10 to 20 $\mu$T and back every 20 seconds. It can be seen that the higher Helmholtz field causes a peak in bioeffect to occur at about 9.5 cm into the tissue. The lower Helmholtz field causes a peak bioeffect to occur at about 13 cm into the tissue. The net effect (shown in FIG. 6) is that the bioeffective region is broader than that plotted above in FIG. 5 for a constant peak Helmholtz field.

It can readily be seen that, upon reading this application, any one skilled in the art of creating EM fields can conceive of many modifications of this setup that will cause the two alternating on/off fields to be reasonably close in magnitude at some region within the tissue, with any degree of broadening required.

To restate the above, (1) I have described above a Helmholtz pair with a single smaller coil in the plane of one of the coils creating an inhomogeneous field across the body (Being in the plane of the Helmholtz is not necessary for the smaller coil, however, it appears convenient for many applications). The Helmholtz pair and the single coil are turned on alternately on time scales of about 0.1 to 2 seconds. The cells in the tissue volume where the magnitude of the EM fields is nearly the same (within about 25%) experience a relatively unchanging field strength, thus, the magnetic field is sensed by these cells and induces a biological effect. The other regions receive a field that varies at intervals that are too short, and therefore, the cells do not sense a biologically modifying field.

(2) Another possible embodiment of this method is the same as in 1, except one can use a small coil in the plane of each coil of the Helmholtz pair. If the fields of the two small coils are phased to oppose each other this would produce a smaller region where the fields of the Helmholtz and smaller coils would be close in value and therefore would produce a smaller EM field induced bioeffect region.

(3) Another embodiment would be the same as in (2) except for two orthogonal double pairs. The use of orthogonal Helmholtz coils (with or without the smaller coils) has the very special advantage of inducing a more uniform electric field within organs. This is important because it is the induced electric field and not the direct EM field cell interaction that induces the bio-effects described in this application. Two orthogonal coil systems would induce electric fields in an organ where a single field would not. Thus, as the one second on/off fields alternate, for example every 10 to 20 seconds, regions of an organ not affected by one orientation would be affected by the orthogonal orientation.

(4) The same as in (1) or (2) except that the coils can rotate around an axis orthogonal to the axis through the center of the coils.

(5) Two orthogonal Helmholtz pairs can be used in which the electrical current in one coil of each pair is adjustable relative to the current in the other coil of the pair. This creates two approximately uniformly decreasing fields across the body, which overlap at one point. This point can be adjusted by varying the relative currents in the coils of each pair. Each pair is turned on alternately to produce a biologically undetectable field in all regions except at and near the overlap.

(6) Any of the above with specially designed coil shapes which can be chosen either physically or electrically.

Devices of Increased Complexity

The ideas presented in this application for focusing the biological effect must meet the specific condition that there be a combination of two fields that have intensities within 25% of each other within the targeted volume. For example, intensities of 100 and 75 would be within 25% of each other. This condition is independent of the orientation or polarization of these fields. It is known by the applicant that the orientation of the fields should be chosen for optimum biological effectiveness in the targeted volume. The smaller the size of the targeted volume, the sharper the field spatial variation needs to be. The EM field magnitudes should vary by at least 50% outside the targeted volume.

Examples to Demonstrate the Use of the Described Apparatus and Methods of Applying EM Field in Cancer Therapy There are two general methods and accompanying devices for application of an EM field to a target volume of tissue adjuvant to radiation therapy.

1. From the Exterior of the Body

This utilizes apparatus and methods to physically direct the appropriate EM field to the tumor target volume.

Prior to application of cancer therapy, the location of the tumor/target volume and the relative locations and types of normal tissues are determined by diagnostic imaging and other medical techniques. Using this information, and, perhaps, methods similar to those employed in radiation therapy planning, external (fiducial) marks can be placed on the patient surface to provide a reference coordinate system for targeting the tumor volume within the body. Using this, external EM field devices can be designed and applied which target the appropriate tissue with the appropriate exposure to improve the therapeutic advantage.

For example, an external EM field system, consisting or one or more coils, could be designed to precisely apply EM fields with the appropriate biological effectiveness to the desired internal tissue volumes. Coil systems used to stimulate nerve firing (Ueno and Matsuda, 1993) or quadrupole (Essele and Stuchly, 1993) might be appropriate.

Device design will depend upon the location of the target in the body. For target volumes close to or on the surface (e.g., skin tumors), simple coils combined with a Helmholtz coils configuration will be sufficient to induce the appropriate biological effect. The strongest measured fields are close to the winding of the coil with a sharp decrease towards the coil center. Single coils present a very sharp decrease of the induced EM field close to the coil plane. They act as dipoles. Quadrupoles can also replace the previous single coils. A quadrupole is made by placing adjacent to each other two coils with currents flowing in opposite directions. The calculated EM field induced by quadrupoles exhibits a spatial peak along an axis perpendicular to the plane of the quadrupoles whose origin is at the crossing of the windings. This centered peak can be utilized for my present focusing technology.

In order to preserve this peak and eliminate the existence of side lobes, these windings can be partially shielded with a metal suitable for magnetic shielding (FIGS. 16, 17, 18). A metal suitable for magnetic shielding can be represented by "$\mu$-metal," and this representation is used hereinafter. Calculations done for this configuration show the presence of the centered EM field peak and the absence of the side lobes. An advantage of using quadrupoles is the ability to access deeper targets within the body of the patient. The use of one quadrupole in a uniform field, however, will still be limited to a large volume. For example, with good shielding, using a combination of a quadrupole and Helmholtz configuration, focusing at 5 cm deep under the skin can be achieved for a volume of approximately 3 cm×7 cm×10 cm. The latter dimension can be minimized to a 3 cm×7 cm×7 cm volume by using a co-planar double quadrupole configuration with an alternating on/off EM field of the quadrupoles, with the two quadrupoles placed at 90° from each other (spatial quadrature) or 3 cm×3 cm×3 cm if the quadrupoles are not coplanar.

Focusing can also be achieved by replacing the Helmholtz coil configuration with a non-co-planar second quadrupole, preferably in spatial quadrature from the first quadrupole, with the only condition that the two symmetry axes intersect in the center of the targeted volume. The two quadrupoles can be placed anywhere, but preferably not in close proximity to each other to limit the induced fields overlap. A modification of the quadrupole structure can be designed with two coils placed on a sphere in spatial quadrature. Using shielding similar to that for the previous quadrupole, calculations of the induced EM field show that the configuration is similar to that of the co-planar double quadrupole. This configuration will simplify the design of a focusing instrumentation for surface and deeper diseases.

These EM field-shaping techniques described above may be combined with time- and magnitude-dependent exposure combination techniques, detailed elsewhere in this patent application.

The concept of treatment planning will be a very important consideration. Computer models or treatment plans may be generated which detail the placement of coils on or near the outside of the body and the characteristics of the EM field within selected volumes of tumor target and other normal tissues. Combining this with bioeffect data for the different tissues, specific applications can be planned and implemented along with other cancer therapies.

For long term EM field exposures a wearable coil and battery system can easily be designed by those skilled in the art.

2. From Inside the Body

This procedure operates via body cavities (intra-cavitary) or directly into tissues (interstitial) via apparatus inserted specifically for EM field or for other cancer treatment purposes.

Targeting considerations will be worked out prior to treatment in treatment planning sessions. Then, devices (e.g., specially designed coils) could be inserted into the body volume containing the tumor, or body volumes containing normal tissue to be spared, for direct application of the appropriate EM field to achieve the improvement in therapeutic advantage. This could be done alone or in combination with external applications. Ferromagnetic materials might be used in conjunction with these applications to concentrate the magnetic fields, applied either within or outside of the body, in a chosen region For example: A device for sensitizing colorectal tumors using rectally inserted devices could be envisioned. In this case, the maximum field strength at the surface of the coil could be directly applied to the region of colon being treated. Or, for prostate cancer, a device could be designed to be inserted trans-urethrally into the prostate, near the tumor site, to stimulate greater therapeutic sensitivity within the prostate disease, while a different device could be inserted rectally for stimulating tissue protection of the rectal wall, a predominant limiting normal tissue in some forms of prostate therapy (e.g., radiation, hyperthermia).

Further Details Applying to Use of EM Fields with Radiation Therapy (RT)

A fundamental principle of RT is that the more dose that can be delivered to a tumor, the more likely it will be cured. In order to accomplish this, there are two fundamental techniques commonly used for applying ionizing radiation in the clinic. Each of these will be listed and an accompanying technique for using adjuvant EM field suggested:

1. Radiation therapy takes advantage of targeting tumor volumes using x-ray (or gamma) beams from different directions that overlap predominantly in the tumor target volume. This limits the dose to the normal tissues between the surface of the body and the tumor to that which is delivered from any one direction, while the tumor volume receives the dose from all directions. This improves the therapeutic advantage.

In a similar way, EM field application can be selectively applied in a manner that the magnitude and duration of the field is most appropriate for down-regulation in the region of the tumor target volume. In this way, the tumor region can be sensitized in preference to the normal tissue. Since a margin of normal tissue around any tumor volume (0.5–1 cm) is conventionally considered to be part of the therapy region, an abrupt transition of the EM field appropriate for down-regulation to that which is not down-regulating at the boundary of the tumor is not imperative. Note that the targeting by the x-ray fields is accurate to about 2 mm.

2. Radiation therapy treatments are divided into multiple fractions to take advantage of the relative inability of tumor cells to repair sub-lethal radiation damage compared to normal tissue. These fractions are normally delivered 5 days per week, although many exceptions to this schedule exist.

The appropriate use of EM fields will therefore probably require multiple applications to continually sensitize or re-sensitize the tumor volume. These applications may be in the form of EM field boosts to maintain the down-regulation within the tumor volume, extended re-application over weekends, or some other schedule not yet recognized.

Additionally, EM fields may be found to be beneficially applied during the period of response of the tumor and normal tissue cells which occurs during or between treatments to further the improvement of the therapeutic advantage.

Chemotherapy

As described above, in a similar manner, chemicals and drugs are used for the purpose of destroying or modifying cancer cells for the purpose of therapy. It is expected that prior to or after the start of chemotherapy, exposure to the proper EM field will improve the cytotoxic potential of these drugs and possibly be synergistic with other actions of drugs as well, such as those which might enhance the effect of radiation.

Multi-modality Therapy

Increasing tumor cell killing with adjuvant therapies is a well-known technique in the art. This is accomplished, for example in RT, by adding drugs or other forms of treatment which kill cancer cells themselves and/or separately or synergistically increase the cells' sensitivity to radiation.

It is envisioned that adjuvant EM field application will promote the combined capabilities of multi-modality treatments. The down-regulation of protective mechanisms within cells tends to make them sensitive to most if not all forms of deleterious stimuli. Therefore, EM field exposures would be expected to complement the application of therapies working together and improve the overall effect of the multiple therapies.

Significance of Blood Vessel (Endothelial) Cells within a Treatment Volume as a Target for Sensitization The ability of a cancer tumor to grow is highly dependent on the supply of oxygen and nutrients provided by the blood vessels. Targeting blood vessel cells within and around a tumor for eradication has been recognized to be a significant goal in cancer treatment (Korner et al., 1993; Qi et al., 1998; Martin and Fischer, 1984. Blood vessel cells are of the same general type (endothelial cells) for any tumor, suggesting that any therapeutic improvement from application of EM field to endothelial cells would potentially be applicable in any tumor type.

In contrast, the cells from different tumors are of different histological types and may have different responses to the EM field applications, just as they tend to be differentially responsive to all other forms of treatment. Therefore, it may be necessary that somewhat different EM field intensities would be needed to most effectively modify different tumor cell responses. This could also be the case in treating different types of tissue and other disease states.

Targeting Normal Tissues for Protection

In addition to the presently presented EM field application for sensitizing the tumor volume, it is also possible to apply an EM field for protecting normal tissues. EM exposures necessary to cause protection are vastly different from those necessary to de-protect or make a cell less resistant to deleterious stimuli. For example, using a 60 Hz, 8 $\mu$T EM field, it requires 20 minutes of exposure to provide protection and over 40 hours to induce a reduced resistance in certain tissues. Therefore, my present invention could be used advantageously in combination with previous art (Litovitz U.S. Pat. No. 5,968,527) which predicts only beneficial effects.

For example, after sensitizing the tumor volume with long term EM exposures focused as detailed above, the following could be done. The Helmholtz coil system which was placed outside the body could be activated to apply an EM field (8 $\mu$T) for a short time (20 min). This would protect the normal tissue throughout the region of the field of the Helmholtz coil but would not affect the region of the tumor whose stress response system had been down-regulated by the long term EM exposure. If the x-ray beam were then applied, the normal tissue would be more resistant and the tumor tissue less resistant to the damaging effect of the x-radiation. Applying the x-ray beam from different directions, overlapping on the tumor, would cause the normal tissue to be further protected in preference to the tumor. In this way, more dose could be delivered to the tumor before the limiting tolerance of the normal tissue was reached.

Discussion of FIGS. 7–18

FIGS. 7–18 represent instrumentation examples for focusing biological effects with specific combinations of induced EM fields on spatial targets.

How to produce low-level, alternating magnetic fields of a given magnitude, polarization, frequency and time dependence within a chosen spatial volume has been described above. The instrumentation is designed to produce two low-level, alternating EM fields with the same frequency to cause a biological effect within cells and tissues. The first coil configuration represents the primary coils and the second coil configuration may be referred to as the secondary coils. When fields are applied from both coils, for full bio-effectiveness, the magnitude of each field must be equal to within 25%. A second condition is that the on time for the primary coils is the off time for the secondary coils, and the off time for the primary coils is the on time for the secondary coils.

Some designs of this instrumentation are given in the following examples with reference to FIGS. 7–18, showing increasing complexity of conception and design. In the following examples, coil configurations may be parallel, coaxial or perpendicular. If focusing cannot be achieved for the whole target, instrumentation can be adapted for scanning the target with progressive adjustments of the focusing parameters. In the Figures, the "Focusing Area" is not intended to be an exact description of the bioeffective region. It is meant to be only an approximate representation of that region.

Instrumentation Examples Using Regular Coils

FIG. 7—General Instrumentation, Example 1

A primary Helmholtz coil configuration (coils 10 and 12) induces a mostly-uniform field between the coils. A secondary coil 14 is placed on the same axis as the primary coils, driven to produce an EM field of the same frequency, with a magnitude decreasing from the coil plane. The secondary field magnitude 16 is represented as a function of the distance from the secondary coil and compared with the magnitude 18 of the uniform field induced by the Helmholtz coil configuration. The secondary field magnitude decreases with the distance from the secondary coil passing through the critical values of 125% and 75% of the Helmholtz coil induced field within a specific region. This region is defined by adjusting the intensity of the current within the secondary coil that controls the field strength within the coil plane and the gradient of the EM field. The bio-effect will be active within this focus area region 20 where the target 22 should be located. The focus of the bio-effect is then adjustable. It can be noted that the primary Helmholtz configuration can also be modified to provide a field gradient to sharpen the region of bio-effectiveness when intensity in the coils are set differently.

FIG. 8—General Instrumentation, Example 2

A primary Helmholtz coil configuration (coils 10 and 12) induces a mostly-uniform cylindrical field between the coils. A secondary coil 24 is placed on an axis 26 perpendicular to the primary axis 28 to produce an EM field of the same frequency with a magnitude decreasing from the coil plane. The secondary field magnitude is represented with the distance from the secondary coil and compared with the magnitude of the uniform field induced by the Helmholtz coil configuration. The secondary field magnitude decreases with the distance from the secondary coil passing through the critical values of 125% and 75% of the Helmholtz coil induced field within a specific region. This region is defined by adjusting the intensity of the current within the secondary coil that controls the field strength within the coil plane and the gradient of the magnetic field. The bio-effect will be active within this region where the target 22 should be located. The focus of the bio-effect is then adjustable. It can be noted that the primary Helmholtz configuration can also be modified to provide a field gradient to sharpen the region of bio-effectiveness when intensity in the coils are set differently.

FIG. 9—General Instrumentation, Example 3

Given the information conveyed by reference characters in FIGS. 7 and 8, the legends alone in the following Figures will suffice to provide a clear understanding of the following figures. Both of the single primary and secondary coils induce fields with the same characteristics and decreasing strengths as the distance from the coil increases. The plane of the secondary coil is placed perpendicular to the primary coil axis. In FIG. 9, both of the primary and secondary field strengths decrease to be within 25% from each other to induce the bio-effect within a specific target region. This region is defined by adjusting the intensity of the primary coil or the intensity of the secondary coil to thus control the field strength within the coil plane and the gradient of the EM field. The bio-effect will be active within this region where the target should be located. The focus of the bio-effect is then adjustable.

FIG. 10—General Instrumentation, Example 4

As shown in FIG. 10, two Helmholtz coil configurations are placed with axes perpendicular to form the primary and secondary settings. The primary setting is a classical Helmholtz configuration with a uniform field between coils. The secondary configuration is a modified Helmholtz configuration where the intensity of each coil is different inducing a spatial gradient for the magnetic field between the two coils. The spatial intersection where the strength of the secondary EM field is within 25% of that of the uniform primary field will be the region with the bio-effectiveness. This region is defined by adjusting the current intensity of one or both coils of the secondary modified Helmholtz coil configuration controlling the field gradient and by adjusting the primary uniform field if necessary. The bio-effect will be active within this region where the target should be located. The focus of the bio-effect is then adjustable. It can be noted that the primary Helmholtz configuration can also be modified as the secondary Helmholtz configuration to provide a field gradient to sharpen the region of bio-effectiveness. In a Helmholtz configuration, the current through both coils is to be in the same direction around the axis of the coils.

FIG. 11—Complex Device, Example 1

Instrumentation designs of increased complexity are provided for instrumentation exterior (FIGS. 11–14) or interior (FIG. 15) to the body. The device of FIG. 11 utilizes the concept of FIG. 10 with two conventional coil settings: a Helmholtz coil configuration and a secondary coil setting for focusing on the targeted volume. Coil rotation about an axis 33 and adjustments of the parameters of the second setting may be used to scan the targeted region. In FIG. 11 areas numbered 30 and 32 represent" the arm openings in the patient vest, and the triangular area 34 represents the collar opening of the patient vest. The number 36 shows a chair where the patient can sit so as to not tire the patient during the exposure. Lines 38, 40 and 42 represent the sides of the patient vest. Lines 43, 44, 46, 48, 50 and 52 represent the pants and shoes of the patient.

FIG. 12—Complex Device, Example 2

This instrumentation is more simplified than FIG. 11, utilizing the concept of FIG. 9, with only two coils with adjustable parameters (e.g., coil configuration and currents) to focus the bio-effect on the targeted volume. The lines in FIG. 12 corresponding to those in FIG. 11 have the same meanings. The lines 54 with the dots 56 at the lower ends represent a guiding limiting frame for the geometric adjustments of the coils.

FIG. 13—Complex Device, Example 3

This configuration utilizes the concept of FIG. 8 with the possible design of a portable device such as a vest. Focusing the bio-effect is achieved by adjusting either the vertical coil setting parameters or the single coil parameters. The construction within circle 58 represents the connecting closure design for the coil 24. The letter "C" represents an electrical connector allowing the current "I" to pass along the coil. This connector can be opened mechanically to take off the vest. Two wires are connected from each side of the connector "C" towards the circle numbered 60. The construction within 60 represents the previously discussed wiring connected to a power supply with safety grounding protection.

FIG. 14—Complex Device, Example 4, Configuration examples of focusing with double inverted circular coils with or without conventional coils This figure shows a set of design configurations (A, B and C) that utilize quadrupoles such as the inverted quadrupoles used for nerve stimulation as mentioned elsewhere in the present application. (A quadrupole is a combined system of two similar coils or dipoles). These inverted quadrupoles are more complex than single coils as known to those skilled in the art of producing EM fields. The field induced by quadrupoles presents a larger gradient than that induced by single coils. The use of quadrupoles instead of single coils will be more efficient for focusing in smaller regions. The present configurations are utilizing the concepts presented in FIGS. 8, 9 and 10. The focusing of the bio-effect on the targeted volume is achieved by adjusting parameters (e.g., current, or angle between the coils) of the inverted quadrupoles to produce the desired EM fields described in FIGS. 8, 9 and 10.

FIG. 15—Complex Device, Example 5

This figure shows designs that utilize either inverted quadrupoles or non-inverted quadrupoles. View A is an example of a focusing device using a non-inverted eight coil configuration for internal use. Use of a ferromagnetic kernel within each coil can improve the magnetic field intensity, reducing the probe size. View B is an example of a focusing device using an inverted eight coil configuration for internal use. Use of a ferromagnetic kernel within each coil can improve the magnetic field intensity, reducing the probe size. View C shows one or the other of the devices of Views A and B mounted on endoscopic tubing, which may also have sensors for probe placement (optical fiber, light, other device). The present configuration will utilize the concept of FIG. 9 or 14. The strength of the quadrupole induced EM fields can be enhanced with ferromagnetic kernels. This amplification can be utilized to miniaturize the devices for internal use. This device can then be mounted on an endoscopic tubing coupled with other sensors or probes (e.g. for light).

FIG. 16—Quadrupole, Example 1

This figure shows a more complex instrumentation using non-coplanar quadrupoles as a primary and secondary source configuration from the concept of FIG. 9 or as a secondary source configuration from the concept of FIG. 14. This figure shows complex instrumentation with quadrupole settings as a combination of primary and secondary source configurations or as a secondary source configuration. The magnitude of the induced field in the plane perpendicular to the axis Δ on M is represented. The presented quadrupoles are to be shielded with $\mu$-metal tubing (not directly represented in the figure but shown as rectangles 62). Quadrupoles #1 and #2 are in spatial quadrature and also in phase quadrature (quadrupoles are in spatial quadrature when they are spatially placed at 90° from each other and they are powered with a 90° phase shift). The figure also shows the magnitude of the EM field induced by a single shielded quadrupole in the plane perpendicular to the symmetric axis of the coil originated by the point M, the field magnitude being expressed in relative units. If both quadrupoles are on at the same time, the total field will be elliptically polarized. The superposition of a uniform field (FIG. 10) or a field with a gradient (FIG. 10) will then provided an intersection region where all alternating fields will be within 25% from each other to induce a full bio-effectiveness. If the quadrupoles are alternatively on and off, only the fields within 25% of each other will be bio-effective and they can be used with or without supplemental coil configurations.

FIG. 17—Quadrupole, Example 2

This figure shows complex instrumentation using co-planar quadrupoles as a primary source configuration or as a secondary source configuration. The concept is the same then for the FIG. 16. The presented quadrupoles are shielded with $\mu$-metal tubing (not directly represented in the figure but shown as rectangles 62). Quadrupole #1 and #2 are spatially in quadrature and also in phase quadrature. This example is a complex instrumentation with shielded quadrupole settings as a secondary source configuration either with alternating fields or a combination of both fields to create a circular polarized field. The magnitude of the induced field in the plane perpendicular to the axis Δ on M is represented. FIG. 17 also shows the magnitude of the magnetic field resulting from the 25% similarity in the magnitude field induced by each of the quadrupoles. If both quadrupoles are on at the same time the resulting field will be a circularly polarized field. The superposition of a uniform field (FIG. 8) or a field with a gradient (FIG. 8) will provided an intersection volume where all alternating fields will be within 25% from each other to induced a full bio-effectiveness. If the quadrupoles are alternatively on, only the fields within 25% of each other will be biologically active and they can be used with or without supplemental coil configurations.

FIG. 18—Quadrupole, Example 3

The figure shows a more complex instrumentation with the same concept as FIG. 17 using two coils in spatial quadrature over a sphere, shielded with $\mu$-metal tubing away from the winding crossing point. This figure is an example of complex instrumentation with shielded coil settings on a sphere as a secondary source configuration either with alternating fields or a combination of both coil induced fields to create a circular polarized field. The magnitude of the induced field in the plane perpendicular to the axis Δ on M is represented. The figure also shows the magnitude of the induced magnetic field resulting from both coils. This configuration can substitute a quadrupole configuration as in FIG. 14, 15, 16 or 17.

Summary of Apparatus Inventions

To summarize the apparatus (instrumentation) inventions disclosed herein, these embrace apparatus for establishing a plurality of electromagnetic (EM) fields to provide a region of bio-effectiveness in a human or animal body. Means are included to generate a first EM field encompassing in part a region in the body wherein the bio-effectiveness is to be achieved, and means m generate at least one additional EM field also in part encompassing said region. Each of the field generating means includes a means for modulating each field to be at first magnitude for a first period of time and at a second magnitude for a following period of time, with changes occurring within approximately 10 second intervals. Further means are provided for controlling the modulation means to cause the magnitude of the first EM field and the additional EM field at all times to be complimentary in respect of time. Complimentary means that the on and off times fill the total time available: when one is on, the other is off. The net result is that within said region the respective fields will provide a combined field having a predetermined pattern of limited differences in magnitude but outside the region the respective fields will alternate between said first and second magnitudes. Where the magnitudes have limited differences, e.g., within 25% or less of each other, there will be bio-effectiveness. However, the latter will not occur when outside the region the alteration is between said first and second magnitudes. In an exemplary case, the means for generation of the first field may be a pair of Helmholtz coils. The means for generation of said additional field may be a single coil, or it may be another Helmholtz pair of coils. In all cases, the axes of the coils may be at an angle to one another, and the angle may be a right angle. The field generating means for the first EM field and the field generating means for the additional may differ at least to the extent that at least one of the fields will have a magnitude distance gradient (increasing or decreasing magnitude along the axis of the field).

My apparatus inventions may also be described as means for focusing the biological effect on cells, tissues or organs by use of an applied EM field which results from the superimposition of two fields each of which is biologically ineffective when applied separately. The respective fields will be generated from a primary source configuration producing a spatially time varying EM field and from a secondary source configuration producing a spatially uniform time varying EM field of the same frequency and waveform as the primary source configuration. The primary and secondary field amplitudes are to be within 25% of being equal only on the targeted cells, tissues and organs. With the amplitude of each field being high in one period of time, followed by a low amplitude in the next period of time, neither field by itself (outside the focus region) will be biologically effective if the chances in amplitude occur within 10 second or less. However, when both of the fields are present (in the focus region), and the high amplitudes of one of the fields occur during the low amplitude periods of the other field, a composite field will result. This may be of constant amplitude, or may vary up m the aforesaid 25%, and the biological effectiveness will exist. The time varying fields may be uniform (high and low periods of time equal) or not uniform (different time periods). As aforesaid, the cycle times may be up to ten seconds, e.g., 5 seconds high and 5 seconds low, preferably 2 seconds high and two seconds low. Preferably, the magnitude of the exposure from each of the source configurations should be no less than 2 microTesla and no greater than 2000 microTesla. The EM field magnitudes preferably may correspond to a radiative energy of at least 1.0 mW/cm squared.

My focusing apparatus may also have source configurations which comprise 2 quadrupoles which provide maximum fields along the symmetry axis thereof, with the field from one quadrupole is high (on) for a maximum time of 5 seconds (preferably 2) when the field from the other quadrupole is low (off) for a maximum period of 5 seconds (preferably 2). The quadrupoles may be coaxial. The quadrupoles may have partially shielded windings, which may be shielded away from the axis thereof. The secondary source configuration may be comprised of 2 quadrupoles in spatial and phase quadrature to provide a maximum circularly polarized field along the symmetry axis thereof, in which case the field is high (on) for a maximum of 5 seconds (preferably 2 seconds).

Also embraced within my inventions is apparatus for use in anti-cancer treatments, comprising means for exposing both normal and diseased tissues to EM fields for a minimum of 20 minutes (preferably for at least 1 hour), with the field exposure ending at a maximum of 10 hours (preferably 1 hour) prior to treatment with therapeutic agents. The magnitude of the exposures from the EM fields is dependant on the field type used, with a preferred level of no less than 2 microTesla and no greater than 2000 microTesla. Means may be included for administering the EM fields in conjunction with prior focusing onto the diseased tissue alone.

My inventions also include apparatus for exposure of EM fields to tissue, which comprise means for generating circular polarized fields for a minimum of 20 minutes and a maximum of 10 hours, the generating means including two EM field source configurations in different configurations.

Consideration of Temperatures

The procedures described in this application are not causing any temperature changes which are biologically meaningful according to what is presently understood. While hyperthermia can produce similar effects, the methods described herein do not rely on hyperthermia to create the effects. The use of hyperthermia has been demonstrated to be very unreliable and very difficult to apply, although there have been several decades of research and clinical trials in this area.

REFERENCES CITED

Aquino D A, Capello E, Weissteiin J, Sanders V, Lopez C, Tourtellotte W W, Brosnan C F, Raine C S, Norton W T, "Multiple sclerosis: altered expression of 70- and 27-jDa heat shock proteins in lesions and myelin," *J. Neuropathol. Exp. Neurol.* 1997;56(6):664–672.

Birnbaum G, Kotilinek L, "Heat shock or stress proteins and their role as auto-antigens in multiple sclerosis," *Ann. NY Acad. Sci.* 1997;835:157–167.

Blank M, Khorkova O, Goodman R, "Changes in polypeptide distribution stimulated by different levels of electromagnetic and thermal stress," *Bioelectrochemistry and Bioenergetics* 1994;33:109–114

Boehneke W H, Dahlke A, Zollner T M, Sterry W, "Differential expression heat shock protein 70 (HSP70) and heat shock cognate proteins 70 (HSC70) in human epidermis," *Arch. Dermatol. Res.* 1994;287(1):68–71.

Borrelli M J, Stafford D M, Karczewski L A, Rausch C M, Lee Y J and Corry P M. "Thermotolerance expression in mitotic CHO cells without increased translation of heat shock proteins," *J Cell Physiol.* 1988;169:420–8.

Cadossi R, Zucchini P, Emilia G, Franceschi C, Cossaaarizza A, Santantonio M, Mandolini G, Torelli G, "Effect of low frequency low energy pulsing electromagnetic fields on mice injected with cyclophosphamide," *Exp. Hematol.* 1991;19:196–201.

Chang B K, Huang A T, Joines W T, "Inhibition of DNA synthesis and enhancement of the uptake and action of methotrexate by low-power-density mucrowave radiation in L1210 leukemic cells," *Cancer Res.* 1980;40: 1002–1005.

Currie R W, Karmazyn M, Kloc M, Mailer K, "Heat-shock response is associated with enhanced postischemic ventricular recovery" *Circ. Res.* 1988;63:543–549

Detlavs I, Dombrovska L, Turauska A, Shkirmante B, Slutskii L, "Experimental study of the effects of radiofrequency electromagnetic fields on animals with soft tissue wounds," *Sci. Total. Environ.* 1996;180:35–42

Di Carlo A L, Farrell J M, Litovitz T A, "Myocardial protection conferred by electromagnetic fields,) *Circulation* 1999;99:813–816

Di Carlo A L, Hargis M T, Penafiel L M, Litovitz T A, "Short-Term Magnetic Field Exposures (60 Hz) Induce Protection Against Ultraviolet Radiation Damage," *Int. J. Radiat. Biol.* 1998;75:1541–1550

Dindar H, Renda N, Barlas M, Akinay A, Yazgan E, Tincer T, Cakmak M, Konkan R, Gokcora I H, Yucesan S, "The effect of electromagnetic field stimulation on corticosteroids-inhibited intestinal wound healing," *Tokai. J. Exp. Clin. Med.* 1993;18:49–55

Donnelly T J, Sievers R E, Vissern F L, Welch W J, Wolfe C L, "Heat shock protein induction in rat hearts. A role for improved myocardial salvage after ischemia and reperfusion?," *Circulation* 1992;85:769–778

Essele K P, Stuchly M A, "Coil optimization for neural stimulation with magnetic field," in *Electricity and Magnetism in Biology and Medicine,* Blank M, Ed. San Francisco Press, Inc. CA. p. 736–7, 1993.

Fitzsimmons R J, Farley J, Adey W R, Baylink D J, "Embryonic bone matrix formation is increased after exposure to a low-amplitude capacitively coupled electric field, in vitro," *Biochim. Biophys. Acta* 1986;882:51–56

Fuks Z, Persaud R S, Alfieri A, McLaughlin M, Ehleister D, Schwartz J L, Seddon A P, Cordon-Cardo C, Haimovitz-Friedman A, "Basic fibroblast growth factor protects endothelial cells against radiation-induced programmed cell death in vitro and in vivo," *Cancer Res.* 1994;54:2582–90.

Goodman R, Blank M, Lin H, Dai R, Khorkova O, Soo L, Weisbrot D, Henderson A, "Increased levels of HSP70 transcripts induced when cells are exposed to low frequency electromagnetic fields," *Bioelectrochemistry and Bioenergetics* 1994;33:115–120

Gordon, S A, Hoffman, R A, Simmons, R L and Ford, H R. "Induction of heat shock protein 70 protects thymocytes against radiation-induced apoptosis," *Arch. Surg.* 1997; 132:1277–82.

Han L, Lin H, Head M, Jin M, Blank M, Goodman R, "Application of magnetic field-induced heat shock protein 70 for presurgical cytoprotection," *J. Cell Biochem.* 1998;71:577–583.

He L and Fox M H. "Variation of heat shock protein 70 through the cell cycle in HL-60 cells and its relationship to apoptosis," *Exp. Cell Res.* 1997;232:64–71.

Hutter M M, Sievers R E, Barbosa V, Wolfe C L, "Heat-shock protein induction in rat hearts. A direct correlation between the amount of heat-shock protein induced and the degree of myocardial protection," *Circulation* 1994;89:355–360

Iwaki K, Chi S H, Dillmann W H, Mestril R, "Induction of HSP70 in cultured rat neonatal cardiomyocytes by hypoxia and metabolic stress," *Circulation* 1993;87:2023–2032

Kang K I, Bouhouche I, Fortin D, Baulieu E E, Catelli M G, "Luciferase activity and synthesis of Hsp70 and Hsp90 are insensitive to 50 Hz electromagnetic fields," *Life Sci.* 1998;63:489–97.

Korner G, Deutsch V R, Vlodavsky I, Eldor A, "Effects of ionizing irradiation on endothelial cell transglutaminase," *FEBS Lett.* 1993;330:41–5.

Lin H, Opler M, Head M, Blank M, Goodman R, "Electromagnetic field exposure induces rapid, transitory heat shock factor activation in human cells" *J. Cell Biochem.* 1997;66 :482–488

Martin D F, Fischer J J, "Radiation sensitivity of cultured rabbit aortic endothelial cells," *IJROBP* 1984;10:1903–6.

Matsumoto H, Hayashi S, Shioura H, Ohtsubo T, Nishida T, Kitai R, Ohnishi T, Kano E, "Suppression of heat-induced p53 accumulation and activation by CDDP or x-rays in human glioblastoma cells," *Int. J. Oncol.* 1998;13(4):741–7.

McCleary V L, Akers T K, Aasen G H, "Low magnetic field effects on embryonic bone growth," *Biomed. Sci. Instrum.* 1991;27:205–217

McMillan D R, Xiao X, Shao L, Graves K, Benjamin I J, "Targeted disruption of heat shock transcription factor 1 abolishes thermotolerance and protection against heat-inducible apoptosis," *J. Biol. Chem.* 1998;273:7523–8.

Mestril R, Chi S H, Sayen M R, O'Reilly K, Dillmann W H, "Expression of inducible stress protein 70 in rat heart myogenic cells confers protection against simulated ischemia-induced injury," *J. Clin. Invest.* 1994;93:759–767

Mestril R, Dillmann W H, "Heat shock proteins and protection against myocardial ischemia," *J. Mol. Cell Cardiol.* 1995;27:45–52

Morimoto R, Fodor E, "Cell-specific expression of heat shock proteins in chicken reticulocytes and lymphocytes," *J. Cell Biol.* 1984;99:1316–1323

Omote Y, Hosokawa M, Komatsumoto M, Namieno T, Nakajima S, Kubo Y, Kobayashi J, "Treatment of experimental tumors with a combination of a pulsing magnetic field and an antitumor drug," *Jpn. J. Cancer Res.* 1990;81:956–961.

O'Rourke J F, Mothersill C E, Seymour C B, Tipton K F, "X-irradiation- and carcinogen-induced proteins in cultured CHO cells," *Biochem. Soc. Trans.* 1992;20(1):74S.

Pasquinelli P, Petrini M, Mattii L, Galimberti S, Saviozzi M, Malvaldi G, "Biological effects of PEMF (pulsing electromagnetic field): An attempt to modify cell resistance to anticancer agents," *J. Environ. Pathol. Toxicol. Oncol.* 1993; 12(4):193–197.

Qi F, Sugihara T, Hattori Y, Yarmamoto Y, Kanno M, Abe K, "Functional and morphological damage of endothelium in rabbit ear artery following irradiation with cobalt 60," *Br. J. Pharmacol.* 1998;123:653–60.

Ritossa F M, "A new puffing pattern induced by heat shock and DNP in *Drosophila,*" *Experentia* 1962;18:571–573

Ruiter G A, Zerp S F, Bartelink H, van Blitterswijk W J, Verheij M, "Alkyl-lysophospholipids activate the SAPK/JNK pathway and enhance radiation-induced apoptosis," *Cancer Res.* 1999;59:2457–63.

Salvatore J R, Blackinton D, Polk C, Mehta S, "Non-ionizing electromagnetic radiation: A study of carcinogenic and cancer treatment potential," *Rev. Environ. Health* 1994;10(3–504):197–207.

Samali A, Cotter, T G, "Heat shock proteins increase resistance to apoptosis," *Exp. Cell Res.* 1996;223(1):163–170.

Schett G, Redlich K, Xu Q, Bizan P, Gröger M, Tohidast-Akrad M, Liener H, Smolen J, Steiner G, "Enhanced expression of heat shock protein 70 (hsp70) and heat shock factor 1 (HSF1) activation in rheumatoid arthritis synovial tissue," *J. Clin. Invest* 1998;102(2):302–311.

Strasser A, Anderson R L, "Bcl-2 and thermotolerance cooperate in cell survival," *Cell Growth Differ.* 1995;6:799–805.

Szigeti G, Banyasz T, Magyar J, Kortvely A, Szigligeti P, Kovacs L, Jednakovits A, Nansai P P, "Effects of Bimoclomal, the novel heat shock protein co-induced, in dog ventricular myocardium," *Life Sci.* 2000;67:73–79.

Tosi P, Visani G, Ottaviani E, Gibellini D, Pellacani A, Tura S, "Reduction of heat-shock protein-70 after prolonged treatment with retinoids: biological and clinical implications," *Am. J. Hematol.* 1997;56(3): 143–150.

Trautinger F, Kokesch C, Herbacek I, Knobler R M and Kindas-Mugge I, "Over expression of the small heat shock protein, hsp27, confers resistance to hyperthermia, but not to oxidative stress and UV-induced cell death, in a stably transfected squamous cell carcinoma cell line," *J Photochem. Photobiol. B* 1997;39:90–5.

Tyrrell R M, "UV activation of mammalian stress proteins," *EXS* 1996;77:255–271.

Ueno S, Matsuda T, "Vectorial magnetic stimulation of the human brain," in *Electricity and Magnetism in Biology and Medicine,* Blank M, Ed. San Francisco Press, Inc. CA. p. 733–4, 1993.

Walker D M, Pasini E, Kucukoglu S, Marber M S, Iliodromitis E, Ferrari R, Yellon D M: Heat stress limits infarct size in the isolated perfused rabbit heart. *Cardiovasc. Res.* 1993;27:962–967

Walter R J, Shtil, A A, Roninson I B and Holian O, "60-Hz electric fields inhibit protein kinase C activity and multidrug resistance gene (MDRI) up-regulation," *Rad. Res.* 1997;147:369–75.

Watters D, "Molecular mechanisms of ionizing radiation-induced apoptosis," *Immunol. Cell Biol.* 1999;77:263–71.

Xu M, Wright W D, Higashikubo R and Roti J R, "Intracellular distribution of hsp70 during long duration moderate hyperthermia," *Int. J. Hyperthermia* 1998;14:211–25.

What is claimed is:

1. A method of targeting and enhancing therapeutic or palliative treatments for diseased tissues or organs including, without limitation, physical, chemical, radiative or gene therapies applied for the treatment and prevention of diseases, which method comprises the step of modulating response protective elements in cells, tissues or organs with selected time exposures of electromagnetic (EM) fields having frequencies within a range of approximately 10 Hz to approximately 5 GHz, wherein the frequencies and time exposures are selected to maintain pretreatment temperature of diseased tissues or organs, wherein time and magnitude of the exposure are dependent on the size of the diseased tissues or organs so as to enhance the endogenous cellular protective responses of normal tissues and/or suppress the endogenous cellular protective responses of diseased tissues.

2. A method as in claim 1 wherein the disease is cancer.

3. A method as in claim 2 wherein the EM field treatment is administered prior to treatment with anti-cancer agents.

4. A method as in claim 3 wherein said EM field exposures are administered over a period of a minimum of 2 days, with a minimum of one exposure each day, with each exposure duration lasting a minimum of 20 minutes.

5. A method as in claim 4 wherein the EM exposures are administered over a period of 4 days.

6. A method as in claim 4 wherein each exposure duration is 1 hour.

7. A method as in claim 2 wherein the EM field treatment is administered both prior to and following treatment with anti-cancer agents.

8. A method as in claim 7 wherein the EM field exposures are administered over a period of a minimum of 2 days both prior to and following treatment with anti-cancer agents, with a minimum of 1 exposure each day, with each exposure duration lasting a minimum of 20 minutes.

9. A method as in claim 8 wherein the EM field exposures are administered over a period of 4 days.

10. A method as in claim 8 wherein the duration of each exposure lasts 1 hour.

11. A method as in claim 1 wherein the disease is any autoimmune dysfunction.

12. A method of targeting and enhancing therapeutic or palliative treatments including, without limitation, physical, chemical, radiative or gene therapies applied for the treatment and prevention of diseases, which method comprises the step of modulating response protective elements in cells, tissues or organs with selected time exposures of electromagnetic (EM) fields having frequencies within a range of approximately 10 Hz to approximately 5 0Hz, wherein time and magnitude of the exposure are dependent on the size of the diseased tissues or organs so as to enhance the endogenous cellular protective responses of normal tissues and/or suppress the endogenous cellular protective responses of diseased tissues, wherein the disease is any autoimmune dysfunction and wherein the EM field exposures are done at least 5 days per week, with a minimum of 1 exposure each day, with each exposure duration lasting a minimum of 20 minutes.

13. A method as in claim 12 wherein the EM field exposures are done 7 days per week.

14. A method as in claim 12 wherein each exposure duration lasts 1 hour.

15. A method of establishing a plurality of EM fields to provide a region of bioeffectiveness in a human or animal body, the method comprising the steps of:

generating a first EM field encompassing at least in a part a region in a human or animal body wherein the bio-effectiveness is to be achieved, generating at least one additional EM field also encompassing at least in part said region, modulating the first field to cause it to be at a first magnitude for a first period of time and at a second magnitude for a following period of time, with changes occurring within approximately 10 second intervals, modulating the additional field to cause it to be at a first magnitude for a first period of time and at a second magnitude for a following period of time, with changes occurring within approximately 10 second intervals, and controlling the modulations to cause the magnitude of the first EM field and the magnitude of the additional field at all give times to be complementary in respect of time, whereby within said region the respective fields will provide a combined field having a predetermined pattern of limited differences in magnitudes but outside the region the respective fields will alternate between said first and second magnitudes.

\* \* \* \* \*